(12) United States Patent
Pantalone et al.

(10) Patent No.: US 7,777,102 B2
(45) Date of Patent: Aug. 17, 2010

(54) SOYBEAN VARIETIES

(75) Inventors: Vincent R. Pantalone, Knoxville, TN (US); Fred L. Allen, Louisville, TN (US); Deborah Landau-Ellis, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 11/672,632

(22) Filed: Feb. 8, 2007

(65) Prior Publication Data

US 2008/0196119 A1 Aug. 14, 2008

(51) Int. Cl.
- A01H 1/00 (2006.01)
- A01H 5/00 (2006.01)
- C12N 15/82 (2006.01)

(52) U.S. Cl. ............... 800/312; 800/260; 800/278; 800/300

(58) Field of Classification Search .......... None
See application file for complete search history.

(56) References Cited

U.S. PATENT DOCUMENTS

| | | | |
|---|---|---|---|
| 4,761,373 A | 8/1988 | Anderson et al. | |
| 4,810,648 A | 3/1989 | Stalker | |
| 5,008,200 A | 4/1991 | Ranch et al. | |
| 5,013,659 A | 5/1991 | Bedbrook et al. | |
| 5,024,944 A | 6/1991 | Collins et al. | |
| 5,126,133 A | 6/1992 | Payne et al. | |
| 5,141,870 A | 8/1992 | Bedbrook et al. | |
| 5,188,960 A | 2/1993 | Payne et al. | |
| 5,304,732 A | 4/1994 | Anderson et al. | |
| 5,331,107 A | 7/1994 | Anderson et al. | |
| 5,378,824 A | 1/1995 | Bedbrook et al. | |
| 5,559,223 A | 9/1996 | Falco et al. | |
| 5,605,011 A | 2/1997 | Bedbrook et al. | |
| 5,731,180 A | 3/1998 | Dietrich | |
| 5,767,361 A | 6/1998 | Dietrich | |
| 5,850,016 A | 12/1998 | Jung et al. | |
| 5,885,801 A | 3/1999 | Rao | |
| 5,885,802 A | 3/1999 | Rao | |
| 5,912,414 A | 6/1999 | Falco et al. | |
| 5,928,937 A | 7/1999 | Kakefuda et al. | |
| 5,939,599 A | 8/1999 | Chui et al. | |
| 5,990,389 A | 11/1999 | Rao et al. | |
| 6,063,947 A | 5/2000 | DeBonte et al. | |
| 6,080,913 A | 6/2000 | Tarczynski et al. | |
| 6,096,708 A | 8/2000 | Payne et al. | |
| 6,127,600 A | 10/2000 | Beach et al. | |
| 6,323,392 B1 | 11/2001 | Charne | |
| 6,346,403 B1 | 2/2002 | Rafalski et al. | |
| 6,372,976 B2 | 4/2002 | Damm | |
| 6,420,632 B1 * | 7/2002 | Eby .................. 800/312 | |
| 6,441,274 B1 | 8/2002 | Cahoon et al. | |
| 6,459,019 B1 | 10/2002 | Falco et al. | |
| 6,531,648 B1 | 3/2003 | Lanahan et al. | |
| 6,573,240 B1 | 6/2003 | Payne et al. | |
| 6,624,342 B1 * | 9/2003 | Grimm et al. .......... 800/278 | |
| 6,635,803 B1 * | 10/2003 | Schroeder et al. ....... 800/278 | |
| 6,664,445 B1 | 12/2003 | Falco et al. | |
| 6,737,273 B2 | 5/2004 | Payne et al. | |
| 6,787,683 B1 | 9/2004 | Penna et al. | |
| 6,858,778 B1 | 2/2005 | Jung et al. | |
| 6,982,367 B2 * | 1/2006 | Eby .................... 800/312 | |
| 7,138,568 B2 | 11/2006 | Payne et al. | |
| 2003/0140379 A1 * | 7/2003 | Kumar et al. .......... 800/289 | |
| 2004/0034886 A1 | 2/2004 | Cahoon et al. | |

FOREIGN PATENT DOCUMENTS

| | | |
|---|---|---|
| WO | WO 93/11245 A1 | 6/1993 |
| WO | WO 99/64579 A2 | 12/1999 |
| WO | WO 00/68393 A1 | 11/2000 |
| WO | WO 01/12800 A2 | 2/2001 |
| WO | WO 03/082899 A2 | 10/2003 |

OTHER PUBLICATIONS

Pantalone, et al 2003, Crop Science 43: 1123-1124.*

(Continued)

*Primary Examiner*—David H Kruse
(74) *Attorney, Agent, or Firm*—Saliwanchik, Lloyd & Saliwanchik

(57) ABSTRACT

This application is directed to novel soybean plant varieties, designated 5601TRR-292 (named 'Allen'), 5601TRR-293, and 5601TRR-379. These varieties are glyphosate resistant cultivars, developed from BC3F2 single-plant derivatives of cultivar '5601T'. Also provided herein are seeds of the aforementioned soybean varieties, plants arising therefrom, plant parts of soybean varieties 5601TRR-292, 5601TRR-293, and 5601TRR-379 and to methods for producing a soybean plant produced by crossing these soybean varieties with another soybean plant (as either the male or the female parent). The subject application also provides methods for introducing another transgenic trait or another genetic trait into the disclosed soybean varieties and soybean plants and plant parts produced by those methods. Also disclosed herein are soybean varieties or breeding varieties and plant parts derived from soybean varieties 5601TRR-292, 5601TRR-293, and 5601TRR-379, methods for producing other soybean varieties or plant parts from soybean varieties 5601TRR-292, 5601TRR-293, and 5601TRR-379 soybean plants, varieties, and their parts derived from the practice of such methods. In another aspect, this application provides soybean seeds, plants, and plant parts produced by crossing the soybean varieties 5601TRR-292, 5601TRR-293, and 5601TRR-379 with another soybean variety.

26 Claims, No Drawings

OTHER PUBLICATIONS

Elmore et al 2001, Agronomy Journal 93: 408-412.*

Aono, M. et al. "Paraquat Tolerance of Transgenic *Nicotiana tabacum* with Enhanced Activities of Glutathione Reductase and Superoxide Dismutase" *Plant Cell Physiol.*, 1995, pp. 1687-1691, vol. 36, No. 8.

Datta, S. K. et al. "Herbicide-Resistant Indica Rice Plants from IRRI Breeding Line IR72 After PEG-Mediated Transformation of Protoplasts" *Plant Molecular Biology*, 1992, pp. 619-629, vol. 20.

Elliott, K. J. et al. "Isolation and Characterization of Fruit Vacuolar Invertase Genes from Two Tomato Species and Temporal Differences in mRNA Levels During Fruit Ripening" *Plant Molecular Biology*, 1993, pp. 515-524, vol. 21.

Fisher, D. K. et al. "Starch Branching Enzyme II from Maize Endosperm" *Plant Physiol.*, 1993, pp. 1045-1046, vol. 102.

Frisch, M. et al. "Comparison of Selection Strategies for Marker-Assisted Backcrossing of a Gene" *Crop. Sci.*, 1999, pp. 1295-1301, vol. 39.

Hammock, B. D. et al. "Expression and Effects of the Juvenile Hormone Esterase in a Baculovirus Vector" *Nature*, Mar. 29, 1990, pp. 458-461, vol. 344.

Hattori, J. et al. "An Acetohydroxy Acid Synthase Mutant Reveals a Single Site Involved in Multiple Herbicide Resistance" *Mol. Gen. Genet.*, 1995, pp. 419-425, vol. 246.

Hillel, J. et al. "DNA Fingerprints Applied to Gene Introgression in Breeding Programs" *Genetics*, Mar. 1990, pp. 783-789, vol. 124.

Hospital, F. et al. "Using Markers in Gene Introgression Breeding Programs" *Genetics*, Dec. 1992, pp. 1199-1210, vol. 132.

Knutzon, D. S. et al. "Modification of *Brassica* Seed Oil by Antisense Expression of a Stearoyl-acyl Carrier Protein Desaturase Gene" *Proc. Natl. Acad. Sci.*, Apr. 1992, pp. 2624-2628, vol. 89.

Lee, K. Y. et al. "The Molecular Basis of Sulfonylurea Herbicide Resistance in Tobacco" *The EMBO Journal*, 1988, pp. 1241-1248, vol. 7, No. 5.

Miki, B. L. at al. "Transformation of *Brassica napus* Canola Cultivars with *Arabidopsis thaliana* Acetohydroxyacid Synthase Genes and Analysis of Herbicide Resistance" *Theor. Appl. Genet.*, 1990, pp. 449-458, vol. 80.

Openshaw, S. J. et al. "Marker-Assisted Selection in Backcross Breeding" *Analysis of Molecular Marker Data*, 1994, pp. 41-43.

Pantalone, V. R. et al. "Registration of '5601T' Soybean" *Crop. Sci.*, 2003, pp. 1123-1124, vol. 43.

Pantalone, V. R. et al. "Registration of TN93-99 Soybean Germplasm" *Crop. Sci.*, 2003, p. 1137, vol. 43.

Pen, J. et al. "Production of Active *Bacillus licheniformis* Alpha-Amylase in Tobacco and Its Application in Starch Liquefaction" *Bio/Technology*, Mar. 1992, pp. 292-296, vol. 10.

Shiota, N. et al. "Herbicide-Resistant Tobacco Plants Expressing the Fused Enzyme Between Rat Cytochrome P4501A1 (CYP1A1) and Yeast NADPH-Cytochrome P450 Oxidoreductase" *Plant Physiol.*, 1994, pp. 17-23, vol. 106.

Shiroza, T. et al. "Sequence Analysis of the *Streptococcus mutans* Fructosyltransferase Gene and Flanking Regions" *Journal of Bacteriology*, Feb. 1988, pp. 810-816, vol. 170, No. 2.

Sogaard, M. et al. "Site-Directed Mutagenesis of Histidine 93, Aspartic Acid 180, Glutamic Acid 205, Histidine 290, and Aspartic Acid 291 at the Active Site and Tryptophan 279 at the Raw Starch Binding Site in Barley α-Amylase 1" *The Journal of Biological Chemistry*, Oct. 25, 1993, pp. 22480-22484, vol. 268, No. 30.

Steinmetz, M. et al. "The DNA Sequence of the Gene for the Secreted *Bacillus subtilis* Enzyme Levansucrase and Its Genetic Control Sites" *Mol. Gen. Genet.*, 1985, pp. 220-228, vol. 200.

Gillen, A.M. et al., Uniform Soybean Tests, Southern States, mailed May 21, 2007, pp. 1-201.

Allen, F. L. et al., Soybean Variety Performance Tests in Tennessee, Jan. 2007, pp. 1-70.

UniSouth Genetics, Inc. product sheet for USG Allen, first offered for sale in Apr. 2006, p. 1.

* cited by examiner

SEQUENCE LISTING

<160> NUMBER OF SEQ ID NOS: 182

<210> SEQ ID NO 1
<211> LENGTH: 25
<212> TYPE: DNA
<213> ORGANISM: Artificial
<220> FEATURE:
<223> OTHER INFORMATION: primer

<400> SEQUENCE: 1
gcggggttgt tgatctataa tgtaa                                          25

<210> SEQ ID NO 2
<211> LENGTH: 25
<212> TYPE: DNA
<213> ORGANISM: Artificial
<220> FEATURE:
<223> OTHER INFORMATION: Primer

<400> SEQUENCE: 2
gcgggtttgg attttataat gtgat                                          25

<210> SEQ ID NO 3
<211> LENGTH: 17
<212> TYPE: DNA
<213> ORGANISM: Artificial
<220> FEATURE:
<223> OTHER INFORMATION: primer

<400> SEQUENCE: 3
gcgcgacctt aatgata                                                   17

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
gcgcccaaag cttaaaattt aata                                           24

<210> SEQ ID NO 5
<211> LENGTH: 27
<212> TYPE: DNA
<213> ORGANISM: Artificial
<220> FEATURE:
<223> OTHER INFORMATION: primer

<400> SEQUENCE: 5
gcgtgcttca aaccaacaaa caactta                                        27

<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
gcggtttgca gtacgtacct aaaataga                                       28

<210> SEQ ID NO 7
<211> LENGTH: 21

```
<212> TYPE: DNA
<213> ORGANISM: Artificial
<220> FEATURE:
<223> OTHER INFORMATION: primer

<400> SEQUENCE: 7
cgtttcattc ccatgccaat a                                              21

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
cccgcatctt tttcaaccac                                                20

<210> SEQ ID NO 9
<211> LENGTH: 28
<212> TYPE: DNA
<213> ORGANISM: Artificial
<220> FEATURE:
<223> OTHER INFORMATION: primer

<400> SEQUENCE: 9
atcccattgt agtgcattta tagtgacg                                       28

<210> SEQ ID NO 10
<211> LENGTH: 28
<212> TYPE: DNA
<213> ORGANISM: Artificial
<220> FEATURE:
<223> OTHER INFORMATION: primer

<400> SEQUENCE: 10
gcgggtaacc tattttttat gcttctgt                                       28

<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11
gcaaatgaag aaaagatgga tt                                             22

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
taaagcgatg gttgaagaaa g                                              21

<210> SEQ ID NO 13
<211> LENGTH: 28
<212> TYPE: DNA
<213> ORGANISM: Artificial
<220> FEATURE:
<223> OTHER INFORMATION: primer

<400> SEQUENCE: 13
```
gcgaagagct acatctaaca caattcaa	28

<210> SEQ ID NO 14
<211> LENGTH: 28
<212> TYPE: DNA
<213> ORGANISM: Artificial
<220> FEATURE:
<223> OTHER INFORMATION: primer

<400> SEQUENCE: 14
gcgttaagca cggtcatatt ttctcata	28

<210> SEQ ID NO 15
<211> LENGTH: 19
<212> TYPE: DNA
<213> ORGANISM: Artificial
<220> FEATURE:
<223> OTHER INFORMATION: primer

<400> SEQUENCE: 15
caacacccta gcatagtca	19

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
agcaggtatg aaatgaaatt	20

<210> SEQ ID NO 17
<211> LENGTH: 23
<212> TYPE: DNA
<213> ORGANISM: Artificial
<220> FEATURE:
<223> OTHER INFORMATION: primer

<400> SEQUENCE: 17
cgcttgccca aaaattaata gta	23

<210> SEQ ID NO 18
<211> LENGTH: 25
<212> TYPE: DNA
<213> ORGANISM: Artificial
<220> FEATURE:
<223> OTHER INFORMATION: primer

<400> SEQUENCE: 18
ccattctcca acctcaatct tatat	25

<210> SEQ ID NO 19
<211> LENGTH: 26
<212> TYPE: DNA
<213> ORGANISM: Artificial
<220> FEATURE:
<223> OTHER INFORMATION: primer

<400> SEQUENCE: 19
taaaaattaa aatactagaa gacaac	26

<210> SEQ ID NO 20
<211> LENGTH: 20
<212> TYPE: DNA
<213> ORGANISM: Artificial

```
<220> FEATURE:
<223> OTHER INFORMATION: primer

<400> SEQUENCE: 20
tggcattaga aaatgatatg                                              20

<210> SEQ ID NO 21
<211> LENGTH: 27
<212> TYPE: DNA
<213> ORGANISM: Artificial
<220> FEATURE:
<223> OTHER INFORMATION: primer

<400> SEQUENCE: 21
gcgaaatttg gaaatgacat cttagaa                                      27

<210> SEQ ID NO 22
<211> LENGTH: 27
<212> TYPE: DNA
<213> ORGANISM: Artificial
<220> FEATURE:
<223> OTHER INFORMATION: primer

<400> SEQUENCE: 22
gcgacgggag aaattggatg tgaagaa                                      27

<210> SEQ ID NO 23
<211> LENGTH: 22
<212> TYPE: DNA
<213> ORGANISM: Artificial
<220> FEATURE:
<223> OTHER INFORMATION: primer

<400> SEQUENCE: 23
ctcctcctgc gcaacaacaa ta                                           22

<210> SEQ ID NO 24
<211> LENGTH: 19
<212> TYPE: DNA
<213> ORGANISM: Artificial
<220> FEATURE:
<223> OTHER INFORMATION: primer

<400> SEQUENCE: 24
gggggatcta ggccatgac                                               19

<210> SEQ ID NO 25
<211> LENGTH: 19
<212> TYPE: DNA
<213> ORGANISM: Artificial
<220> FEATURE:
<223> OTHER INFORMATION: primer

<400> SEQUENCE: 25
accgcaactc actcacctt                                               19

<210> SEQ ID NO 26
<211> LENGTH: 19
<212> TYPE: DNA
<213> ORGANISM: Artificial
<220> FEATURE:
<223> OTHER INFORMATION: primer

<400> SEQUENCE: 26
gcgcccaatt aacagaaac                                               19
```

<210> SEQ ID NO 27
<211> LENGTH: 24
<212> TYPE: DNA
<213> ORGANISM: Artificial
<220> FEATURE:
<223> OTHER INFORMATION: primer

<400> SEQUENCE: 27
tattataaaa atcaatgcga aagg                                          24

<210> SEQ ID NO 28
<211> LENGTH: 27
<212> TYPE: DNA
<213> ORGANISM: Artificial
<220> FEATURE:
<223> OTHER INFORMATION: primer

<400> SEQUENCE: 28 cttttaata agcccaaata attacat                                        27

<210> SEQ ID NO 29
<211> LENGTH: 24
<212> TYPE: DNA
<213> ORGANISM: Artificial
<220> FEATURE:
<223> OTHER INFORMATION: primer

<400> SEQUENCE: 29
gcgggatcca ccatgtaata tgtg                                          24

<210> SEQ ID NO 30
<211> LENGTH: 21
<212> TYPE: DNA
<213> ORGANISM: Artificial
<220> FEATURE:
<223> OTHER INFORMATION: primer

<400> SEQUENCE: 30
gcgcactaac cctttattga a                                             21

<210> SEQ ID NO 31
<211> LENGTH: 18
<212> TYPE: DNA
<213> ORGANISM: Artificial
<220> FEATURE:
<223> OTHER INFORMATION: primer

<400> SEQUENCE: 31
acctcatttt ggcataaa                                                 18

<210> SEQ ID NO 32
<211> LENGTH: 23
<212> TYPE: DNA
<213> ORGANISM: Artificial
<220> FEATURE:
<223> OTHER INFORMATION: primer

<400> SEQUENCE: 32
ttggaaaaca agtaataata aca                                           23

<210> SEQ ID NO 33
<211> LENGTH: 24
<212> TYPE: DNA
<213> ORGANISM: Artificial
<220> FEATURE:
<223> OTHER INFORMATION: primer -continued

<400> SEQUENCE: 33
gcgcgatggg ctgttggttt ttat                                         24

<210> SEQ ID NO 34
<211> LENGTH: 28
<212> TYPE: DNA
<213> ORGANISM: Artificial
<220> FEATURE:
<223> OTHER INFORMATION: primer

<400> SEQUENCE: 34
gcgcatacga tttggcattt ttctattg                                     28

<210> SEQ ID NO 35
<211> LENGTH: 22
<212> TYPE: DNA
<213> ORGANISM: Artificial
<220> FEATURE:
<223> OTHER INFORMATION: primer

<400> SEQUENCE: 35
agtcgaagat acacaattag at                                           22

<210> SEQ ID NO 36
<211> LENGTH: 23
<212> TYPE: DNA
<213> ORGANISM: Artificial
<220> FEATURE:
<223> OTHER INFORMATION: primer

<400> SEQUENCE: 36
cttttagaca caaatttatc act                                          23

<210> SEQ ID NO 37
<211> LENGTH: 17
<212> TYPE: DNA
<213> ORGANISM: Artificial
<220> FEATURE:
<223> OTHER INFORMATION: primer

<400> SEQUENCE: 37
gcgctggcct ttagaac                                                 17

<210> SEQ ID NO 38
<211> LENGTH: 26
<212> TYPE: DNA
<213> ORGANISM: Artificial
<220> FEATURE:
<223> OTHER INFORMATION: primer

<400> SEQUENCE: 38
gcgttgtagg aaatttgagt agtaag                                       26

<210> SEQ ID NO 39
<211> LENGTH: 26
<212> TYPE: DNA
<213> ORGANISM: Artificial
<220> FEATURE:
<223> OTHER INFORMATION: primer

<400> SEQUENCE: 39
ggaatgcatg agtattaacc tcttat                                       26

<210> SEQ ID NO 40

```
<211> LENGTH: 27
<212> TYPE: DNA
<213> ORGANISM: Artificial
<220> FEATURE:
<223> OTHER INFORMATION: primer

<400> SEQUENCE: 40
gggctaacga acatgtaact tatcaac                                            27

<210> SEQ ID NO 41
<211> LENGTH: 22
<212> TYPE: DNA
<213> ORGANISM: Artificial
<220> FEATURE:
<223> OTHER INFORMATION: primer

<400> SEQUENCE: 41
ccatcccttc ctccaaatag at                                                 22

<210> SEQ ID NO 42
<211> LENGTH: 25
<212> TYPE: DNA
<213> ORGANISM: Artificial
<220> FEATURE:
<223> OTHER INFORMATION: primer

<400> SEQUENCE: 42
cttccacacc ctagtttagt gacaa                                              25

<210> SEQ ID NO 43
<211> LENGTH: 27
<212> TYPE: DNA
<213> ORGANISM: Artificial
<220> FEATURE:
<223> OTHER INFORMATION: primer

<400> SEQUENCE: 43
gcgtataaag aaaaacgagc atatcat                                            27

<210> SEQ ID NO 44
<211> LENGTH: 28
<212> TYPE: DNA
<213> ORGANISM: Artificial
<220> FEATURE:
<223> OTHER INFORMATION: primer

<400> SEQUENCE: 44
gcgcttataa aggcttgtga aagacact                                           28

<210> SEQ ID NO 45
<211> LENGTH: 26
<212> TYPE: DNA
<213> ORGANISM: Artificial
<220> FEATURE:
<223> OTHER INFORMATION: primer

<400> SEQUENCE: 45
gcgtgtcttc ccaatccatc taatct                                             26

<210> SEQ ID NO 46
<211> LENGTH: 28
<212> TYPE: DNA
<213> ORGANISM: Artificial
<220> FEATURE:
<223> OTHER INFORMATION: primer

<400> SEQUENCE: 46
```

```
gcgactctgc atttctgaat aaattcac                                      28
```

<210> SEQ ID NO 47
<211> LENGTH: 27
<212> TYPE: DNA
<213> ORGANISM: Artificial
<220> FEATURE:
<223> OTHER INFORMATION: primer

<400> SEQUENCE: 47

```
gggattaggt ttatggaagt ttattat                                       27
```

<210> SEQ ID NO 48
<211> LENGTH: 24
<212> TYPE: DNA
<213> ORGANISM: Artificial
<220> FEATURE:
<223> OTHER INFORMATION: primer

<400> SEQUENCE: 48

```
gggtcattaa aacgatcagt aaga                                          24
```

<210> SEQ ID NO 49
<211> LENGTH: 27
<212> TYPE: DNA
<213> ORGANISM: Artificial
<220> FEATURE:
<223> OTHER INFORMATION: primer

<400> SEQUENCE: 49

```
gcgctatgta gattatccaa attacgc                                       27
```

<210> SEQ ID NO 50
<211> LENGTH: 19
<212> TYPE: DNA
<213> ORGANISM: Artificial
<220> FEATURE:
<223> OTHER INFORMATION: primer

<400> SEQUENCE: 50

```
gccacttact gttactcat                                                19
```

<210> SEQ ID NO 51
<211> LENGTH: 25
<212> TYPE: DNA
<213> ORGANISM: Artificial
<220> FEATURE:
<223> OTHER INFORMATION: primer

<400> SEQUENCE: 51

```
gcgtgtacat caaaatggtg tattc                                         25
```

<210> SEQ ID NO 52
<211> LENGTH: 25
<212> TYPE: DNA
<213> ORGANISM: Artificial
<220> FEATURE:
<223> OTHER INFORMATION: primer

<400> SEQUENCE: 52

```
gcgggaggaa ctttgtctca gtaat                                         25
```

<210> SEQ ID NO 53
<211> LENGTH: 21
<212> TYPE: DNA

<210> SEQ ID NO 53
<211> LENGTH: 21
<212> TYPE: DNA
<213> ORGANISM: Artificial
<220> FEATURE:
<223> OTHER INFORMATION: primer

<400> SEQUENCE: 53
tgagcgatca agaagcactt a                                                   21

<210> SEQ ID NO 54
<211> LENGTH: 21
<212> TYPE: DNA
<213> ORGANISM: Artificial
<220> FEATURE:
<223> OTHER INFORMATION: primer

<400> SEQUENCE: 54
tttggatcgc ataacacttt a                                                   21

<210> SEQ ID NO 55
<211> LENGTH: 17
<212> TYPE: DNA
<213> ORGANISM: Artificial
<220> FEATURE:
<223> OTHER INFORMATION: primer

<400> SEQUENCE: 55
agcctccggt atcacag                                                        17

<210> SEQ ID NO 56
<211> LENGTH: 18
<212> TYPE: DNA
<213> ORGANISM: Artificial
<220> FEATURE:
<223> OTHER INFORMATION: primer

<400> SEQUENCE: 56
cctcctttct cccatttt                                                       18

<210> SEQ ID NO 57
<211> LENGTH: 26
<212> TYPE: DNA
<213> ORGANISM: Artificial
<220> FEATURE:
<223> OTHER INFORMATION: primer

<400> SEQUENCE: 57
gcggggtcaa ttagttttcg tcagtt                                              26

<210> SEQ ID NO 58
<211> LENGTH: 25
<212> TYPE: DNA
<213> ORGANISM: Artificial
<220> FEATURE:
<223> OTHER INFORMATION: primer

<400> SEQUENCE: 58
gcgcacggta tataatcgaa cctat                                               25

<210> SEQ ID NO 59
<211> LENGTH: 26
<212> TYPE: DNA
<213> ORGANISM: Artificial
<220> FEATURE:
<223> OTHER INFORMATION: primer

<400> SEQUENCE: 59
tcgtgttaga ttttactgt cacatt                                               26

<210> SEQ ID NO 60
<211> LENGTH: 22
<212> TYPE: DNA
<213> ORGANISM: Artificial
<220> FEATURE:
<223> OTHER INFORMATION: primer

<400> SEQUENCE: 60
aactgcatac cctttgtttg aa                                              22

<210> SEQ ID NO 61
<211> LENGTH: 19
<212> TYPE: DNA
<213> ORGANISM: Artificial
<220> FEATURE:
<223> OTHER INFORMATION: primer

<400> SEQUENCE: 61
tgaccaccat gagttcatt                                                  19

<210> SEQ ID NO 62
<211> LENGTH: 19
<212> TYPE: DNA
<213> ORGANISM: Artificial
<220> FEATURE:
<223> OTHER INFORMATION: primer

<400> SEQUENCE: 62
gggggtggct tttagattc                                                  19

<210> SEQ ID NO 63
<211> LENGTH: 24
<212> TYPE: DNA
<213> ORGANISM: Artificial
<220> FEATURE:
<223> OTHER INFORMATION: primer

<400> SEQUENCE: 63
ttgggttgac cgtgagaggg agaa                                            24

<210> SEQ ID NO 64
<211> LENGTH: 24
<212> TYPE: DNA
<213> ORGANISM: Artificial
<220> FEATURE:
<223> OTHER INFORMATION: primer

<400> SEQUENCE: 64
gcgaaccaca acaacaatc ttca                                             24

<210> SEQ ID NO 65
<211> LENGTH: 26
<212> TYPE: DNA
<213> ORGANISM: Artificial
<220> FEATURE:
<223> OTHER INFORMATION: primer

<400> SEQUENCE: 65
tctggtaaac attcaacttt ttattt                                          26

<210> SEQ ID NO 66
<211> LENGTH: 26
<212> TYPE: DNA
<213> ORGANISM: Artificial
<220> FEATURE:

-continued

<223> OTHER INFORMATION: primer

<400> SEQUENCE: 66
tccaaatatg acatcataaa cttcta                                              26

<210> SEQ ID NO 67
<211> LENGTH: 26
<212> TYPE: DNA
<213> ORGANISM: Artificial
<220> FEATURE:
<223> OTHER INFORMATION: primer

<400> SEQUENCE: 67
cagaaaagga ataataacaa catcac                                              26

<210> SEQ ID NO 68
<211> LENGTH: 28
<212> TYPE: DNA
<213> ORGANISM: Artificial
<220> FEATURE:
<223> OTHER INFORMATION: primer

<400> SEQUENCE: 68
gcgaaaacat aattcacaca aaagacag                                            28

<210> SEQ ID NO 69
<211> LENGTH: 22
<212> TYPE: DNA
<213> ORGANISM: Artificial
<220> FEATURE:
<223> OTHER INFORMATION: primer

<400> SEQUENCE: 69
tgtgggtaaa atagataaaa at                                                  22

<210> SEQ ID NO 70
<211> LENGTH: 18
<212> TYPE: DNA
<213> ORGANISM: Artificial
<220> FEATURE:
<223> OTHER INFORMATION: primer

<400> SEQUENCE: 70
tcattttgaa tcgttgaa                                                       18

<210> SEQ ID NO 71
<211> LENGTH: 26
<212> TYPE: DNA
<213> ORGANISM: Artificial
<220> FEATURE:
<223> OTHER INFORMATION: primer

<400> SEQUENCE: 71
aaatacaagc tttaataaag tgcaga                                              26

<210> SEQ ID NO 72
<211> LENGTH: 23
<212> TYPE: DNA
<213> ORGANISM: Artificial
<220> FEATURE:
<223> OTHER INFORMATION: primer

<400> SEQUENCE: 72
cttacgtttc catagatttc tcg                                                 23

<210> SEQ ID NO 73
<211> LENGTH: 20
<212> TYPE: DNA
<213> ORGANISM: Artificial
<220> FEATURE:
<223> OTHER INFORMATION: primer

<400> SEQUENCE: 73
aattcattta gggagttgat                                               20

<210> SEQ ID NO 74
<211> LENGTH: 20
<212> TYPE: DNA
<213> ORGANISM: Artificial
<220> FEATURE:
<223> OTHER INFORMATION: primer

<400> SEQUENCE: 74
ctagccaatg tcatatgact                                               20

<210> SEQ ID NO 75
<211> LENGTH: 24
<212> TYPE: DNA
<213> ORGANISM: Artificial
<220> FEATURE:
<223> OTHER INFORMATION: primer

<400> SEQUENCE: 75 tcagggtgg acctatataa aata                                           24

<210> SEQ ID NO 76
<211> LENGTH: 20
<212> TYPE: DNA
<213> ORGANISM: Artificial
<220> FEATURE:
<223> OTHER INFORMATION: primer

<400> SEQUENCE: 76
cagtggtggc agatgtagaa                                               20

<210> SEQ ID NO 77
<211> LENGTH: 28
<212> TYPE: DNA
<213> ORGANISM: Artificial
<220> FEATURE:
<223> OTHER INFORMATION: primer

<400> SEQUENCE: 77
gcgcatatga ataggtaagt tgcactaa                                      28

<210> SEQ ID NO 78
<211> LENGTH: 25
<212> TYPE: DNA
<213> ORGANISM: Artificial
<220> FEATURE:
<223> OTHER INFORMATION: primer

<400> SEQUENCE: 78
gcgttttcct acaataatat ttcat                                         25

<210> SEQ ID NO 79
<211> LENGTH: 25
<212> TYPE: DNA
<213> ORGANISM: Artificial
<220> FEATURE:
<223> OTHER INFORMATION: primer

```
<400> SEQUENCE: 79
ttactggccg tgtttacccg tgtaa                                              25

<210> SEQ ID NO 80
<211> LENGTH: 28
<212> TYPE: DNA
<213> ORGANISM: Artificial
<220> FEATURE:
<223> OTHER INFORMATION: primer

<400> SEQUENCE: 80
gcggacgtta taagattttt ttatcatg                                           28

<210> SEQ ID NO 81
<211> LENGTH: 24
<212> TYPE: DNA
<213> ORGANISM: Artificial
<220> FEATURE:
<223> OTHER INFORMATION: primer

<400> SEQUENCE: 81
gcgtgccagg tagaaaaata ttag                                               24

<210> SEQ ID NO 82
<211> LENGTH: 24
<212> TYPE: DNA
<213> ORGANISM: Artificial
<220> FEATURE:
<223> OTHER INFORMATION: primer

<400> SEQUENCE: 82 gcggttttc acttttcaaa attc                                                24

<210> SEQ ID NO 83
<211> LENGTH: 27
<212> TYPE: DNA
<213> ORGANISM: Artificial
<220> FEATURE:
<223> OTHER INFORMATION: primer

<400> SEQUENCE: 83
gcgcttagta atggttccca cagataa                                            27

<210> SEQ ID NO 84
<211> LENGTH: 22
<212> TYPE: DNA
<213> ORGANISM: Artificial
<220> FEATURE:
<223> OTHER INFORMATION: primer

<400> SEQUENCE: 84
gcggtgatat ctagcaacac aa                                                 22

<210> SEQ ID NO 85
<211> LENGTH: 26
<212> TYPE: DNA
<213> ORGANISM: Artificial
<220> FEATURE:
<223> OTHER INFORMATION: primer

<400> SEQUENCE: 85
gcgaatttgg attaattaaa tttatg                                             26

<210> SEQ ID NO 86
<211> LENGTH: 27
```

<212> TYPE: DNA
<213> ORGANISM: Artificial
<220> FEATURE:
<223> OTHER INFORMATION: primer

<400> SEQUENCE: 86
gcgctcggtc ctctcaaata aggtctc                                           27

<210> SEQ ID NO 87
<211> LENGTH: 30
<212> TYPE: DNA
<213> ORGANISM: Artificial
<220> FEATURE:
<223> OTHER INFORMATION: primer

<400> SEQUENCE: 87
ttgcacattc tttttggtaa acagtcataa                                        30

<210> SEQ ID NO 88
<211> LENGTH: 30
<212> TYPE: DNA
<213> ORGANISM: Artificial
<220> FEATURE:
<223> OTHER INFORMATION: primer

<400> SEQUENCE: 88
gttggaggcc atagtcacat taatcttaga                                        30

<210> SEQ ID NO 89
<211> LENGTH: 18
<212> TYPE: DNA
<213> ORGANISM: Artificial
<220> FEATURE:
<223> OTHER INFORMATION: primer

<400> SEQUENCE: 89
gggttatcct ccccaata                                                     18

<210> SEQ ID NO 90
<211> LENGTH: 21
<212> TYPE: DNA
<213> ORGANISM: Artificial
<220> FEATURE:
<223> OTHER INFORMATION: primer

<400> SEQUENCE: 90
atatgggatg ataaggtgaa a                                                 21

<210> SEQ ID NO 91
<211> LENGTH: 20
<212> TYPE: DNA
<213> ORGANISM: Artificial
<220> FEATURE:
<223> OTHER INFORMATION: primer

<400> SEQUENCE: 91
caagctcaag cctcacacat                                                   20

<210> SEQ ID NO 92
<211> LENGTH: 22
<212> TYPE: DNA
<213> ORGANISM: Artificial
<220> FEATURE:
<223> OTHER INFORMATION: primer

<400> SEQUENCE: 92

```
tgaccagagt ccaaagttca tc                                                22
```

<210> SEQ ID NO 93
<211> LENGTH: 28
<212> TYPE: DNA
<213> ORGANISM: Artificial
<220> FEATURE:
<223> OTHER INFORMATION: primer

<400> SEQUENCE: 93

```
gcgttgttgt ttcaaatgta ttttagtt                                          28
```

<210> SEQ ID NO 94
<211> LENGTH: 28
<212> TYPE: DNA
<213> ORGANISM: Artificial
<220> FEATURE:
<223> OTHER INFORMATION: primer

<400> SEQUENCE: 94

```
gcggacggat catcaaacca atcaagac                                          28
```

<210> SEQ ID NO 95
<211> LENGTH: 18
<212> TYPE: DNA
<213> ORGANISM: Artificial
<220> FEATURE:
<223> OTHER INFORMATION: primer

<400> SEQUENCE: 95

```
ggaaagaatc agcaaaat                                                     18
```

<210> SEQ ID NO 96
<211> LENGTH: 19
<212> TYPE: DNA
<213> ORGANISM: Artificial
<220> FEATURE:
<223> OTHER INFORMATION: primer

<400> SEQUENCE: 96

```
cccccacata aataataaa                                                    19
```

<210> SEQ ID NO 97
<211> LENGTH: 27
<212> TYPE: DNA
<213> ORGANISM: Artificial
<220> FEATURE:
<223> OTHER INFORMATION: primer

<400> SEQUENCE: 97

```
gcggcacgag tcaactttct gtttcct                                           27
```

<210> SEQ ID NO 98
<211> LENGTH: 24
<212> TYPE: DNA
<213> ORGANISM: Artificial
<220> FEATURE:
<223> OTHER INFORMATION: primer

<400> SEQUENCE: 98

```
gcggaagaag attttcgttt ttat                                              24
```

<210> SEQ ID NO 99
<211> LENGTH: 20
<212> TYPE: DNA
<213> ORGANISM: Artificial

```
<220> FEATURE:
<223> OTHER INFORMATION: primer

<400> SEQUENCE: 99
cgtcgccatc actatgagaa                                              20

<210> SEQ ID NO 100
<211> LENGTH: 24
<212> TYPE: DNA
<213> ORGANISM: Artificial
<220> FEATURE:
<223> OTHER INFORMATION: primer

<400> SEQUENCE: 100
ccatcttgag cagagtttga agtt                                         24

<210> SEQ ID NO 101
<211> LENGTH: 24
<212> TYPE: DNA
<213> ORGANISM: Artificial
<220> FEATURE:
<223> OTHER INFORMATION: primer

<400> SEQUENCE: 101
gcgatatgct ttgtaagaaa atta                                         24

<210> SEQ ID NO 102
<211> LENGTH: 24
<212> TYPE: DNA
<213> ORGANISM: Artificial
<220> FEATURE:
<223> OTHER INFORMATION: primer

<400> SEQUENCE: 102
gcgcaagccc aaatattaca aatt                                         24

<210> SEQ ID NO 103
<211> LENGTH: 24
<212> TYPE: DNA
<213> ORGANISM: Artificial
<220> FEATURE:
<223> OTHER INFORMATION: primer

<400> SEQUENCE: 103
ctcatgtggt cctacccaga ctca                                         24

<210> SEQ ID NO 104
<211> LENGTH: 26
<212> TYPE: DNA
<213> ORGANISM: Artificial
<220> FEATURE:
<223> OTHER INFORMATION: primer

<400> SEQUENCE: 104
cgctatccct ttgtattttc ttttgc                                       26

<210> SEQ ID NO 105
<211> LENGTH: 21
<212> TYPE: DNA
<213> ORGANISM: Artificial
<220> FEATURE:
<223> OTHER INFORMATION: primer

<400> SEQUENCE: 105
gcgggctttg ccaagaagtt t                                            21
```

<210> SEQ ID NO 106
<211> LENGTH: 20
<212> TYPE: DNA
<213> ORGANISM: Artificial
<220> FEATURE:
<223> OTHER INFORMATION: primer

<400> SEQUENCE: 106
gcggtgaggc tggctataag                                          20

<210> SEQ ID NO 107
<211> LENGTH: 28
<212> TYPE: DNA
<213> ORGANISM: Artificial
<220> FEATURE:
<223> OTHER INFORMATION: primer

<400> SEQUENCE: 107
gcgttttttc aatttaaaga gaattgac                                 28

<210> SEQ ID NO 108
<211> LENGTH: 28
<212> TYPE: DNA
<213> ORGANISM: Artificial
<220> FEATURE:
<223> OTHER INFORMATION: primer

<400> SEQUENCE: 108
gcgtaacttg catgtgtata tcgagatg                                 28

<210> SEQ ID NO 109
<211> LENGTH: 26
<212> TYPE: DNA
<213> ORGANISM: Artificial
<220> FEATURE:
<223> OTHER INFORMATION: primer

<400> SEQUENCE: 109
gcgagtatcc accctttat aataat                                    26

<210> SEQ ID NO 110
<211> LENGTH: 26
<212> TYPE: DNA
<213> ORGANISM: Artificial
<220> FEATURE:
<223> OTHER INFORMATION: primer

<400> SEQUENCE: 110
tctccacgcc accttatttc ctctcc                                   26

<210> SEQ ID NO 111
<211> LENGTH: 20
<212> TYPE: DNA
<213> ORGANISM: Artificial
<220> FEATURE:
<223> OTHER INFORMATION: primer

<400> SEQUENCE: 111
gcgcttccac cacaataaca                                          20

<210> SEQ ID NO 112
<211> LENGTH: 21
<212> TYPE: DNA
<213> ORGANISM: Artificial
<220> FEATURE:
<223> OTHER INFORMATION: primer

<400> SEQUENCE: 112
gcggcagagg actgacagct a								21

<210> SEQ ID NO 113
<211> LENGTH: 28
<212> TYPE: DNA
<213> ORGANISM: Artificial
<220> FEATURE:
<223> OTHER INFORMATION: primer

<400> SEQUENCE: 113
gcgaacaaac tttctataca tgataaca							28

<210> SEQ ID NO 114
<211> LENGTH: 29
<212> TYPE: DNA
<213> ORGANISM: Artificial
<220> FEATURE:
<223> OTHER INFORMATION: primer

<400> SEQUENCE: 114
gcgggtatat ttttgtacat aagttggaa							29

<210> SEQ ID NO 115
<211> LENGTH: 24
<212> TYPE: DNA
<213> ORGANISM: Artificial
<220> FEATURE:
<223> OTHER INFORMATION: primer

<400> SEQUENCE: 115
gcggaattag aactccagta aaga							24

<210> SEQ ID NO 116
<211> LENGTH: 21
<212> TYPE: DNA
<213> ORGANISM: Artificial
<220> FEATURE:
<223> OTHER INFORMATION: primer

<400> SEQUENCE: 116
gcgaggccaa cattgaaaag t								21

<210> SEQ ID NO 117
<211> LENGTH: 23
<212> TYPE: DNA
<213> ORGANISM: Artificial
<220> FEATURE:
<223> OTHER INFORMATION: primer

<400> SEQUENCE: 117
gcggcaaatt gttattgtga gac							23

<210> SEQ ID NO 118
<211> LENGTH: 22
<212> TYPE: DNA
<213> ORGANISM: Artificial
<220> FEATURE:
<223> OTHER INFORMATION: primer

<400> SEQUENCE: 118
ggccagtgtt gagggattta ga							22

<210> SEQ ID NO 119

```
<211> LENGTH: 28
<212> TYPE: DNA
<213> ORGANISM: Artificial
<220> FEATURE:
<223> OTHER INFORMATION: primer

<400> SEQUENCE: 119
gcgagtaacg gtcttctaac aaggaaag                                        28

<210> SEQ ID NO 120
<211> LENGTH: 25
<212> TYPE: DNA
<213> ORGANISM: Artificial
<220> FEATURE:
<223> OTHER INFORMATION: primer

<400> SEQUENCE: 120
gcgtgccctt actctcaaaa aaaaa                                           25

<210> SEQ ID NO 121
<211> LENGTH: 25
<212> TYPE: DNA
<213> ORGANISM: Artificial
<220> FEATURE:
<223> OTHER INFORMATION: primer

<400> SEQUENCE: 121
gcggttgtaa tttaatgaac acatt                                           25

<210> SEQ ID NO 122
<211> LENGTH: 25
<212> TYPE: DNA
<213> ORGANISM: Artificial
<220> FEATURE:
<223> OTHER INFORMATION: primer

<400> SEQUENCE: 122
gcggattttg gactggatta aataa                                           25

<210> SEQ ID NO 123
<211> LENGTH: 29
<212> TYPE: DNA
<213> ORGANISM: Artificial
<220> FEATURE:
<223> OTHER INFORMATION: primer

<400> SEQUENCE: 123
gcgcatatca aattgcatat aaaaatacg                                       29

<210> SEQ ID NO 124
<211> LENGTH: 29
<212> TYPE: DNA
<213> ORGANISM: Artificial
<220> FEATURE:
<223> OTHER INFORMATION: primer

<400> SEQUENCE: 124
gcgggaatat aaaataaaaa tgctcactt                                       29

<210> SEQ ID NO 125
<211> LENGTH: 23
<212> TYPE: DNA
<213> ORGANISM: Artificial
<220> FEATURE:
<223> OTHER INFORMATION: primer

<400> SEQUENCE: 125
```

-continued gcgcctgatt acattatcgc tta                                    23

<210> SEQ ID NO 126
<211> LENGTH: 24
<212> TYPE: DNA
<213> ORGANISM: Artificial
<220> FEATURE:
<223> OTHER INFORMATION: primer

<400> SEQUENCE: 126
gcctttcgtt ctcaaactga gagt                                   24

<210> SEQ ID NO 127
<211> LENGTH: 26
<212> TYPE: DNA
<213> ORGANISM: Artificial
<220> FEATURE:
<223> OTHER INFORMATION: primer

<400> SEQUENCE: 127
gcgatagagc aactggcaaa cttgat                                 26

<210> SEQ ID NO 128
<211> LENGTH: 25
<212> TYPE: DNA
<213> ORGANISM: Artificial
<220> FEATURE:
<223> OTHER INFORMATION: primer

<400> SEQUENCE: 128
gcgaatggag aaaatatgga caaaa                                  25

<210> SEQ ID NO 129
<211> LENGTH: 24
<212> TYPE: DNA
<213> ORGANISM: Artificial
<220> FEATURE:
<223> OTHER INFORMATION: primer

<400> SEQUENCE: 129
gcggcagaga taattgtatt tttg                                   24

<210> SEQ ID NO 130
<211> LENGTH: 28
<212> TYPE: DNA
<213> ORGANISM: Artificial
<220> FEATURE:
<223> OTHER INFORMATION: primer

<400> SEQUENCE: 130
gcgctgccca ctagggaacg aaagatga                               28

<210> SEQ ID NO 131
<211> LENGTH: 23
<212> TYPE: DNA
<213> ORGANISM: Artificial
<220> FEATURE:
<223> OTHER INFORMATION: primer

<400> SEQUENCE: 131
aaatgcaact tacacaactt tat                                    23

<210> SEQ ID NO 132
<211> LENGTH: 24
<212> TYPE: DNA

<210> SEQ ID NO 133
<211> LENGTH: 26
<212> TYPE: DNA
<213> ORGANISM: Artificial
<220> FEATURE:
<223> OTHER INFORMATION: primer

<400> SEQUENCE: 132
tgcttgcttc aatttggatg agtg                                          24

<210> SEQ ID NO 133
<211> LENGTH: 26
<212> TYPE: DNA
<213> ORGANISM: Artificial
<220> FEATURE:
<223> OTHER INFORMATION: primer

<400> SEQUENCE: 133
gcgccaaatg tactttaa attctt                                          26

<210> SEQ ID NO 134
<211> LENGTH: 26
<212> TYPE: DNA
<213> ORGANISM: Artificial
<220> FEATURE:
<223> OTHER INFORMATION: primer

<400> SEQUENCE: 134
gcgggtttag ctaaaatagt tcgtgc                                        26

<210> SEQ ID NO 135
<211> LENGTH: 25
<212> TYPE: DNA
<213> ORGANISM: Artificial
<220> FEATURE:
<223> OTHER INFORMATION: primer

<400> SEQUENCE: 135
ttgggaaata gtgattgagg taaaa                                         25

<210> SEQ ID NO 136
<211> LENGTH: 24
<212> TYPE: DNA
<213> ORGANISM: Artificial
<220> FEATURE:
<223> OTHER INFORMATION: primer

<400> SEQUENCE: 136
aaatccccat tgaatgagaa taag                                          24

<210> SEQ ID NO 137
<211> LENGTH: 24
<212> TYPE: DNA
<213> ORGANISM: Artificial
<220> FEATURE:
<223> OTHER INFORMATION: primer

<400> SEQUENCE: 137
tgccgcgaga ttaatataat ttgt                                          24

<210> SEQ ID NO 138
<211> LENGTH: 24
<212> TYPE: DNA
<213> ORGANISM: Artificial
<220> FEATURE:
<223> OTHER INFORMATION: primer

<400> SEQUENCE: 138
gtgcggcaag aagttgaaat aaag                                          24

<210> SEQ ID NO 139
<211> LENGTH: 27
<212> TYPE: DNA
<213> ORGANISM: Artificial
<220> FEATURE:
<223> OTHER INFORMATION: primer

<400> SEQUENCE: 139
gcgatttctt ccttgaagaa ttttctg                                  27

<210> SEQ ID NO 140
<211> LENGTH: 27
<212> TYPE: DNA
<213> ORGANISM: Artificial
<220> FEATURE:
<223> OTHER INFORMATION: primer

<400> SEQUENCE: 140 gcgcttttc ggctgttatt tttaact                                   27

<210> SEQ ID NO 141
<211> LENGTH: 26
<212> TYPE: DNA
<213> ORGANISM: Artificial
<220> FEATURE:
<223> OTHER INFORMATION: primer

<400> SEQUENCE: 141
gcggtaagtc atggcttttt aatctt                                   26

<210> SEQ ID NO 142
<211> LENGTH: 26
<212> TYPE: DNA
<213> ORGANISM: Artificial
<220> FEATURE:
<223> OTHER INFORMATION: primer

<400> SEQUENCE: 142
gcgcgaggta tggaacctaa ctcaca                                   26

<210> SEQ ID NO 143
<211> LENGTH: 18
<212> TYPE: DNA
<213> ORGANISM: Artificial
<220> FEATURE:
<223> OTHER INFORMATION: primer

<400> SEQUENCE: 143
tgggctagga gtgaccac                                            18

<210> SEQ ID NO 144
<211> LENGTH: 18
<212> TYPE: DNA
<213> ORGANISM: Artificial
<220> FEATURE:
<223> OTHER INFORMATION: primer

<400> SEQUENCE: 144
ggtcaccact caccatca                                            18

<210> SEQ ID NO 145
<211> LENGTH: 28
<212> TYPE: DNA
<213> ORGANISM: Artificial
<220> FEATURE:

```
<223> OTHER INFORMATION: primer

<400> SEQUENCE: 145
gcggtcacga atacaagata aataatgc                                              28

<210> SEQ ID NO 146
<211> LENGTH: 28
<212> TYPE: DNA
<213> ORGANISM: Artificial
<220> FEATURE:
<223> OTHER INFORMATION: primer

<400> SEQUENCE: 146
gcgtgcatgt cagaaaaaat ctctataa                                              28

<210> SEQ ID NO 147
<211> LENGTH: 24
<212> TYPE: DNA
<213> ORGANISM: Artificial
<220> FEATURE:
<223> OTHER INFORMATION: primer

<400> SEQUENCE: 147
gggttaaccg tccacacatc tatt                                                  24

<210> SEQ ID NO 148
<211> LENGTH: 24
<212> TYPE: DNA
<213> ORGANISM: Artificial
<220> FEATURE:
<223> OTHER INFORMATION: primer

<400> SEQUENCE: 148
gacggtttta aacggtaaga aaat                                                  24

<210> SEQ ID NO 149
<211> LENGTH: 20
<212> TYPE: DNA
<213> ORGANISM: Artificial
<220> FEATURE:
<223> OTHER INFORMATION: primer

<400> SEQUENCE: 149 cgcaccccctc atcctatgta                                                      20

<210> SEQ ID NO 150
<211> LENGTH: 24
<212> TYPE: DNA
<213> ORGANISM: Artificial
<220> FEATURE:
<223> OTHER INFORMATION: primer

<400> SEQUENCE: 150
ccaactaatc ccagggactt actt                                                  24

<210> SEQ ID NO 151
<211> LENGTH: 23
<212> TYPE: DNA
<213> ORGANISM: Artificial
<220> FEATURE:
<223> OTHER INFORMATION: primer

<400> SEQUENCE: 151
taatcgagat ttaatagaaa aca                                                   23
```

```
<210> SEQ ID NO 152
<211> LENGTH: 17
<212> TYPE: DNA
<213> ORGANISM: Artificial
<220> FEATURE:
<223> OTHER INFORMATION: primer

<400> SEQUENCE: 152
tggatggaca ttttcag                                                    17

<210> SEQ ID NO 153
<211> LENGTH: 23
<212> TYPE: DNA
<213> ORGANISM: Artificial
<220> FEATURE:
<223> OTHER INFORMATION: primer

<400> SEQUENCE: 153
gcgctaaggg caattttatt caa                                             23

<210> SEQ ID NO 154
<211> LENGTH: 28
<212> TYPE: DNA
<213> ORGANISM: Artificial
<220> FEATURE:
<223> OTHER INFORMATION: primer

<400> SEQUENCE: 154
gcgcagcctg ttcagttttt cttttgtc                                        28

<210> SEQ ID NO 155
<211> LENGTH: 21
<212> TYPE: DNA
<213> ORGANISM: Artificial
<220> FEATURE:
<223> OTHER INFORMATION: primer

<400> SEQUENCE: 155
ttgcacagtt gatttttgtt t                                               21

<210> SEQ ID NO 156
<211> LENGTH: 21
<212> TYPE: DNA
<213> ORGANISM: Artificial
<220> FEATURE:
<223> OTHER INFORMATION: primer

<400> SEQUENCE: 156
gcatcgaatt tctggattta c                                               21

<210> SEQ ID NO 157
<211> LENGTH: 24
<212> TYPE: DNA
<213> ORGANISM: Artificial
<220> FEATURE:
<223> OTHER INFORMATION: primer

<400> SEQUENCE: 157
ctaagcgtga caaacagacc atta                                            24

<210> SEQ ID NO 158
<211> LENGTH: 21
<212> TYPE: DNA
<213> ORGANISM: Artificial
<220> FEATURE:
<223> OTHER INFORMATION: primer
```

```
<400> SEQUENCE: 158
cggccatatc taccaatcag a                                        21

<210> SEQ ID NO 159
<211> LENGTH: 28
<212> TYPE: DNA
<213> ORGANISM: Artificial
<220> FEATURE:
<223> OTHER INFORMATION: primer

<400> SEQUENCE: 159
gcggttacat cttgcaaact aaattaac                                 28

<210> SEQ ID NO 160
<211> LENGTH: 28
<212> TYPE: DNA
<213> ORGANISM: Artificial
<220> FEATURE:
<223> OTHER INFORMATION: primer

<400> SEQUENCE: 160
gcggaatttt gcacataaat taataact                                 28

<210> SEQ ID NO 161
<211> LENGTH: 18
<212> TYPE: DNA
<213> ORGANISM: Artificial
<220> FEATURE:
<223> OTHER INFORMATION: primer

<400> SEQUENCE: 161
gcggacgaat tttccaga                                            18

<210> SEQ ID NO 162
<211> LENGTH: 24
<212> TYPE: DNA
<213> ORGANISM: Artificial
<220> FEATURE:
<223> OTHER INFORMATION: primer

<400> SEQUENCE: 162
gcggggcaac aatatttgaa tcta                                     24

<210> SEQ ID NO 163
<211> LENGTH: 21
<212> TYPE: DNA
<213> ORGANISM: Artificial
<220> FEATURE:
<223> OTHER INFORMATION: primer

<400> SEQUENCE: 163
caatgtgatt agttttggaa a                                        21

<210> SEQ ID NO 164
<211> LENGTH: 21
<212> TYPE: DNA
<213> ORGANISM: Artificial
<220> FEATURE:
<223> OTHER INFORMATION: primer

<400> SEQUENCE: 164
gggttaatgt tgttttttat a                                        21

<210> SEQ ID NO 165
<211> LENGTH: 30
```

<212> TYPE: DNA
<213> ORGANISM: Artificial
<220> FEATURE:
<223> OTHER INFORMATION: primer

<400> SEQUENCE: 165
gcgtagatgc tcaacatcaa cactaatctg                                    30

<210> SEQ ID NO 166
<211> LENGTH: 30
<212> TYPE: DNA
<213> ORGANISM: Artificial
<220> FEATURE:
<223> OTHER INFORMATION: primer

<400> SEQUENCE: 166
gcggacgatg aagaaatata ctattacgaa                                    30

<210> SEQ ID NO 167
<211> LENGTH: 27
<212> TYPE: DNA
<213> ORGANISM: Artificial
<220> FEATURE:
<223> OTHER INFORMATION: primer

<400> SEQUENCE: 167
tggcagcaca cctgctaagg gaataaa                                       27

<210> SEQ ID NO 168
<211> LENGTH: 27
<212> TYPE: DNA
<213> ORGANISM: Artificial
<220> FEATURE:
<223> OTHER INFORMATION: primer

<400> SEQUENCE: 168
gcgaggtggt ctaaaattat tacctat                                       27

<210> SEQ ID NO 169
<211> LENGTH: 26
<212> TYPE: DNA
<213> ORGANISM: Artificial
<220> FEATURE:
<223> OTHER INFORMATION: primer

<400> SEQUENCE: 169
gcgcgcattt tttaagttaa tgttct                                        26

<210> SEQ ID NO 170
<211> LENGTH: 24
<212> TYPE: DNA
<213> ORGANISM: Artificial
<220> FEATURE:
<223> OTHER INFORMATION: primer

<400> SEQUENCE: 170
gcgcgagtta gcgaattatt tgtc                                          24

<210> SEQ ID NO 171
<211> LENGTH: 18
<212> TYPE: DNA
<213> ORGANISM: Artificial
<220> FEATURE:
<223> OTHER INFORMATION: primer

<400> SEQUENCE: 171

```
ggctaacccg ctctatgt                                                  18

<210> SEQ ID NO 172
<211> LENGTH: 19
<212> TYPE: DNA
<213> ORGANISM: Artificial
<220> FEATURE:
<223> OTHER INFORMATION: primer

<400> SEQUENCE: 172
gggccatgca cctgctact                                                 19

<210> SEQ ID NO 173
<211> LENGTH: 22
<212> TYPE: DNA
<213> ORGANISM: Artificial
<220> FEATURE:
<223> OTHER INFORMATION: primer

<400> SEQUENCE: 173
ctggcgaatc aagctttgta ac                                             22

<210> SEQ ID NO 174
<211> LENGTH: 22
<212> TYPE: DNA
<213> ORGANISM: Artificial
<220> FEATURE:
<223> OTHER INFORMATION: primer

<400> SEQUENCE: 174
ccgtgattgc gaagaggata tt                                             22

<210> SEQ ID NO 175
<211> LENGTH: 21
<212> TYPE: DNA
<213> ORGANISM: Artificial
<220> FEATURE:
<223> OTHER INFORMATION: primer

<400> SEQUENCE: 175
gcgtgatttc aatccttttt c                                              21

<210> SEQ ID NO 176
<211> LENGTH: 21
<212> TYPE: DNA
<213> ORGANISM: Artificial
<220> FEATURE:
<223> OTHER INFORMATION: primer

<400> SEQUENCE: 176
gcggttgtcc tgttagaacc t                                              21

<210> SEQ ID NO 177
<211> LENGTH: 21
<212> TYPE: DNA
<213> ORGANISM: Artificial
<220> FEATURE:
<223> OTHER INFORMATION: primer

<400> SEQUENCE: 177
gcgcttttag cgtcgtctgg c                                              21

<210> SEQ ID NO 178
<211> LENGTH: 21
<212> TYPE: DNA
<213> ORGANISM: Artificial
```

-continued

```
<220> FEATURE:
<223> OTHER INFORMATION: primer

<400> SEQUENCE: 178
tacccctctc ttattcttct t                                             21

<210> SEQ ID NO 179
<211> LENGTH: 24
<212> TYPE: DNA
<213> ORGANISM: Artificial
<220> FEATURE:
<223> OTHER INFORMATION: primer

<400> SEQUENCE: 179
gcgtattcag caaaaaaata tcaa                                          24

<210> SEQ ID NO 180
<211> LENGTH: 25
<212> TYPE: DNA
<213> ORGANISM: Artificial
<220> FEATURE:
<223> OTHER INFORMATION: primer

<400> SEQUENCE: 180
ttatcgcacg tgtaaggaga caaat                                         25

<210> SEQ ID NO 181
<211> LENGTH: 29
<212> TYPE: DNA
<213> ORGANISM: Artificial
<220> FEATURE:
<223> OTHER INFORMATION: primer

<400> SEQUENCE: 181
gcgctttcaa aaagtaacaa ttaatgaaa                                     29

<210> SEQ ID NO 182
<211> LENGTH: 27
<212> TYPE: DNA
<213> ORGANISM: Artificial
<220> FEATURE:
<223> OTHER INFORMATION: primer

<400> SEQUENCE: 182
gcgggaattg gttaatctca tcgtgac                                       27
```

SOYBEAN VARIETIES

FIELD OF INVENTION

This invention is in the field of soybean breeding, specifically relating to soybean varieties, designated 5601TRR-292 (named 'Allen'), 5601TRR-293, and 5601TRR-379.

BACKGROUND OF INVENTION

Soybean (*Glycine max*), is an important and valuable field crop and breeders continue to develop stable soybean varieties that produce high yields. The soybean is an important source for vegetable oil and protein meal (with the extracted oils being used for cooking oil, margarine, and salad dressings). Soybean is also used as a food source for both animals and humans.

SUMMARY OF INVENTION

This application provides a number of novel soybean plant varieties, designated 5601TRR-292 (named 'Allen'), 5601TRR-293, and 5601TRR-379. These varieties are glyphosate resistant cultivars, developed from BC3F2 single-plant derivatives of cultivar '5601T'. Also provided herein are seeds of the aforementioned soybean varieties, plants arising therefrom, plant parts of soybean varieties 5601TRR-292, 5601TRR-293, and 5601TRR-379 and to methods for producing a soybean plant produced by crossing these soybean varieties with another soybean plant (as either the male or the female parent).

This invention also relates to methods for introducing another transgenic trait or another genetic trait into the disclosed soybean varieties. The subject invention also relates to soybean plants and plant parts produced by those methods. This subject invention also provides soybean varieties or breeding varieties and plant parts derived from soybean varieties 5601TRR-292, 5601TRR-293, and 5601TRR-379, to methods for producing other soybean varieties or plant parts from soybean varieties 5601TRR-292, 5601TRR-293, and 5601TRR-379 and to the soybean plants, varieties, and their parts derived from the practice of such methods. In another aspect, this application provides soybean seeds, plants, and plant parts produced by crossing the soybean varieties 5601TRR-292, 5601TRR-293, and 5601TRR-379 with another soybean variety.

DEFINITIONS

Certain definitions used in the specification are provided below.

An "allele" is one or more alternative forms of a genetic sequence within an organism. In a diploid cell or organism, the two alleles of a given sequence typically occupy corresponding loci on a pair of homologous chromosomes.

"Backcrossing" is the crossing of a progeny variety back with one of the parental varieties one or more times.

A cross to introduce new genetic material into a plant for the development of a new variety is referred to as a "breeding cross".

The terms "BC1F1", "BC2F1" and "BC3F1" refer to the hybrid obtained from the first, second, and third backcross generations, respectively to the recurrent parental variety. The term "cell" includes a plant cell, whether isolated, in tissue culture or incorporated in a plant or plant part.

The term "embryo" refers to a small plant contained within a mature seed.

"Plant" includes an immature or mature whole plant, including a plant from which seed or grain or anthers have been removed. Seed or embryo that will produce the plant is also considered to be the plant. As used herein, the term "plant parts" includes leaves, stems, roots, root tips, anthers, seed, grain, embryo, pollen, ovules, flowers, cotyledon, hypocotyl, pods, shoots and stalks, tissues and/or cells obtained from the plant.

DETAILED DESCRIPTION OF INVENTION

5601TRR-292 (named 'Allen'), 5601TRR-293, and 5601TRR-379 are glyphosate resistant cultivars, developed from BC3F2 single-plant derivatives of cultivar '5601T' (Pantalone et al., 2003a). The soybean varieties disclosed herein are adapted to growth in Tennessee and areas having similar growing climates.

These glyphosate resistant conversion lines were developed via molecular marker recurrent parent genome recovery, utilizing 89 polymorphic simple sequence repeat (SSR) markers spanning the 20 molecular linkage groups (MLG) of the soybean genome. The SSR markers enabled the identification of specific BC1F1, BC2F1, and BC3F1 individual plants, whose DNA profiles had the greatest commonality with the genome of the recurrent parent 5601T. This strategy enabled rapid accomplishment of full recovery of all 89 markers, capturing the high yielding 5601T genome. Addition of the gene for resistance to glyphosate (ROUNDUP) herbicide was accomplished through hybridization from the donor line TN93-99RR [which was a glyphosate resistant derivative of 1N93-99 (Pantalone et al., 2003b)], and phenotypic selection was conducted for progeny plants which survived glyphosate treatments up to twice recommended field rates.

At least 2500 seeds of Soybean Varieties 5601TRR-292, 5601TRR-293, and 5601TRR-379 have been or will be deposited with The National Collection of Industrial, Marine and Food Bacteria (NCIMB Ltd., Ferguson Building, Craibstone Estate, Bucksburn Aberdeen Scotland AB21 9YA). The Soybean Variety 5601TRR-292 was accepted for deposit on Jan. 25, 2007 as Deposit No. NCIMB 41461. Access to these deposits will be available during the pendency of the application to the Commissioner of Patents and Trademarks and persons determined by the Commissioner to be entitled thereto upon request. Upon allowance of any claims in the application, the Applicant will make the deposits available to the public pursuant to 37 C.F.R. §1.808. These deposits of will be maintained in the depository, which is a public depository, for a period of 30 years, or 5 years after the most recent request, or for the enforceable life of the patent, whichever is longer, and will be replaced if it becomes nonviable during that period.

The 5601TRR-lines are highly similar in their characteristics to the backcross recurrent parent cultivar, 5601T, with the notable exception that the conversion lines are resistant to glyphosate herbicide. Each of the lines has white flowers, gray pubescence, tan podwall, a determinate growth habit, and exhibit good lodging resistance. The seeds are yellow with smooth seed coats and buff hila.

DNA Fingerprinting was performed on Allen, 5601TRR-293, 5601TRR-379, as well at the 5601T recurrent parent and the cultivars 'Essex' and 'Williams-82' (Table 1). Essex and Williams are major ancestors contributing to current southern and northern USA cultivars, respectively. Williams-82 is the cultivar currently utilized by the USA Department of Energy (DOE) soybean sequencing project, and is also the basis for the soybean expressed sequence tag (EST) collection.

Ninety-one SSR marker loci were screened among 19 of soybean's 20 MLG. Table 1 lists the linkage group, the position in centimorgans (cM) from the teleomere, the SSR locus name, type of allele for 5601T (EX=Essex type, WM=Williams-82 type, NP=no polymorphism, TN=5601T showed a unique allele type), numerical values are base pair (bp) lengths of migrated PCR amplified product fragments of the genome using a Beckman-Coulter CEQ Genetic Analysis System with molecular primers synthesized with Beckman fluorescent labeled dyes; a dot indicates that no discernable fragment was detected at the time the reaction was run.

Allen can be distinguished molecularly from 5601T. For example, on MLG B2, at Satt168, Allen showed a fragment length at 224 bp whereas 5601T showed fragments of 224 and 230 bp at the same locus; at Satt070, Allen showed a fragment length at 162 bp whereas 5601T showed fragments of 147 and 162 bp at the same locus; at Satt 474 Allen showed a fragment length at 259 bp whereas 5601T showed a fragment length of 237 bp at the same locus. Differences at other MLG loci are also apparent (Table 1).

Allen can also be distinguished from its backcross sister lines (5601TRR-293 and 5601TRR-379). For example, on MLG D1a at Satt179 Allen showed a fragment length at 182 bp whereas 5601TRR-293 showed a fragment length of 179 bp at the same locus; on MLG B2 at Satt534 Allen showed a fragment length at 189 bp whereas 5601TRR-379 showed a fragment lengths of 186 and 189 bp at the same locus. Differences among the glyphosate resistant cultivars at other MLG loci are also apparent (Table 1).

In one aspect of the invention, a soybean plant characterized by molecular and physiological data obtained from a representative sample of the disclosed varieties as deposited with the National Collections of Industrial Food and Marine Bacteria in Aberdeen, Scotland. Further provided by the invention is a soybean plant formed by the combination of the disclosed soybean plant varieties or plant cells obtained therefrom with another soybean plant or cell.

As recognized by, and generally known to, those skilled in the art, plants can be identified by their genotype. Typically, the plants are characterized through a genetic marker profile to identify plants of the same variety or a related variety. Genetic markers can also be used to determine or validate a pedigree. Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs) are non-limiting examples of techniques that can be used to identify the genetic markers within a plant's genotype and the characterization of the plants disclosed herein is not limited to a particular set of markers. However, one non-limiting example of markers suitable for use in identification of the soybean varieties (and derivatives thereof) of the subject invention are identified in Table 2.

SSR profiles of 5601TRR-292, 5601TRR-293, and 5601TRR-379 can be used to identify progeny plants obtained from these parental plants since the progeny plants typically comprise the same homozygous alleles. The genetic marker profile of an F1 progeny, however, is typically the sum of the parent plants, e.g., if one parent was homozygous for allele x at a particular locus, and the other parent homozygous for allele y at that locus, then the F1 progeny will be xy (heterozygous) at that locus. Subsequent generations of progeny produced by selection and breeding are expected to be of genotype x (homozygous), y (homozygous), or xy (heterozygous) for that locus position. When the F1 plant is selfed or sibbed for successive filial generations, the locus should be either x or y for that position.

Soybean varieties 5601TRR-292, 5601TRR-293, and 5601TRR-379 also constitute new varieties into which new traits can also be introduced. These traits can be introduced genetically via transformation (e.g., the introduction of a desired trait transgenically) or by plant breeding programs. In one exemplary plant breeding program, a backcross can produce a plant with a desired trait. Molecular marker assisted breeding or selection may be utilized to reduce the number of backcrosses necessary to achieve the backcross conversion (see, for example, Frisch et al., 1999; Hillel et al., 1990; Hospital et al., 1992; Openshaw et al., 1994). Desired traits (also referred to as "traits of interest" or genes of interest") that may be transferred through a backcross or transgenic manipulation of the plant include, but are not limited to, sterility (nuclear and cytoplasmic), restoration of fertility, nutritional enhancements, drought tolerance, nitrogen utilization, altered fatty acid profile, low phytate, industrial enhancements, disease resistance (bacterial, fungal or viral), insect resistance and herbicide resistance. In addition, an insertion site, such as an FRT site, Lox site or other site specific integration site, may be inserted by backcrossing and utilized for direct insertion of one or more genes of interest into a specific plant variety. As set forth in the subject invention, one or more transgenes can be inserted into a given variety such that a combination of phenotypic traits is exhibited by the plants.

Selection of progeny containing the trait of interest is accomplished by direct selection for a trait associated with the allele. Along with selection for the trait of interest, progeny are selected for the phenotype of the recurrent parent. One method for adding or modifying a trait in soybean varieties 5601TRR-292, 5601TRR-293, and 5601TRR-379 comprises crossing plants grown from 5601 TRR-292, 5601 TRR-293 or 5601 TRR-379 seed with plants of another soybean variety that exhibit a desired trait, selecting F1 progeny plants that comprise the desired trait to produce selected F1 progeny plants. The F1 progeny plants are then crossed with 5601TRR-292, 5601TRR-293, and 5601TRR-379 plants to produce backcrossed progeny plants which are then selected for the desired trait. This process can be repeated 2 to 6 (or more) times.

As discussed above, the subject invention provides transgenic soybeans comprising soybean varieties 5601TRR-292, 5601TRR-293, and/or 5601TRR-379 into which transgenes have been introduced. Transgenic soybeans can contain one or more transgenes that provide a specific trait into the aforementioned soybean varieties. Anywhere from one to 20 (or more) additional transgenes can be introduced into soybean varieties 5601TRR-292, 5601TRR-293 and 5601TRR-379 to form transgenic soybean plants.

Thus, the subject invention also provides a method for producing transgenic soybeans comprising transforming any one of soybean plant varieties 5601TRR-292, 5601TRR-293 or 5601TRR-379 with a transgene that confers a desired trait into the plant. Also provided by the subject invention are the plants produced by this method. As would be apparent to those skilled in the art, the additional traits introduced into the transgenic plants can be resistance to additional herbicides (e.g., in addition to glyphosate resistance or new constructs that confer glyphosate resistance), insect resistance, disease resistance, freeze tolerance, drought tolerance, altered antioxidant content, modified fatty acid profiles, or altered carbohydrate metabolism. Non-limiting examples of additional herbicides to which resistance can be conferred are sulfonylurea, imidazolinone, glufosinate, phenoxy proprionic acid, cyclohexone, triazine, and benzonitrile.

Genes encoding a desired trait are generally known in the art. Non-limiting examples of such genes include: 1) plant disease resistance genes; 2) *Bacillus thuringiensis* toxins, derivatives thereof, etc (see, for example, U.S. Pat. Nos. 7,138,568, 6,737,273, 6,573,240, 6,096,708, 5,188,960, and/or 5,126,133 which are each hereby are incorporated by reference for this purpose; 3) insect-specific hormones or pheromones (such as an ecdysteroid and juvenile hormone, see Hammock et al., 1990); 4) genes encoding proteins conferring resistance to sulfonylurea or imidazolinone herbicide (see, for example, Lee et al., 1988; Miki et al., 1990; and U.S. Pat. Nos. 5,605,011; 5,013,659; 5,141,870; 5,767,361; 5,731,180; 5,304,732; 4,761,373; 5,331,107; 5,928,937; and 5,378,824 [each of which is hereby incorporated by reference in their entireties]); 5) genes encoding resistance to triazine or other herbicides (see, for example, U.S. Pat. No. 4,810,648; Hattori et al., 1995; Shiota et al., 1994; Aono et al., 1995; and Datta et al., 1992; 6) genes that result in: modified fatty acid profiles (e.g., down-regulation of stearoyl-ACP desaturase to increase stearic acid content of the plant [Knultzon et al., 1992, and WO 99/64579]), or elevated oleic acid via FAD-2 gene modification and/or decreasing linolenic acid via FAD-3 gene modification [see U.S. Pat. Nos. 6,063,947; 6,323,392; 6,372,965 and/or WO 93/11245), or altered of linolenic or linoleic acid content [see, for example, WO 01/12800], or altered the antioxidant or carbohydrate content of the plant or plant cell/part (see, for example, U.S. Pat. No. 6,531,648 or 6,858,778; Shiroza et al., 1988; Steinmetz et al., 1985; Pen et al., 1992; Elliot et al., 1993; Sogaard et al., 1993 (site-directed mutagenesis of barley alpha-amylase gene); and Fisher et al., 1993); U.S. Pat. No. 6,787,683, U.S. Patent Application Publication 2004/0034886, WO 00/68393, or WO 03/082899, each of which is hereby incorporated by reference in their entirety; or 7) altered amino acid profiles (see, for example, U.S. Pat. Nos. 6,127,600, 6,080,913, 5,990,389, 5,850,016, 5,885,802, 5,885,801, 6,664,445, 6,459,019, 6,441,274, 6,346,403, 5,939,599, 5,912,414, or 5,559,223, each of which is hereby incorporated by reference in its entirety).

Tissue culture of soybeans, and the regeneration of plants therefrom, is well known and numerous publications are available in this regard (see, for example, U.S. Pat. Nos. 5,024,944 and 5,008,200, the disclosures of which are hereby incorporated herein in their entirety). Thus, another aspect of this invention is to provide cells (e.g., from protoplasts or other regenerable cells) which upon growth and differentiation produce soybean plants having the physiological and morphological characteristics of soybean varieties 5601TRR-292, 5601TRR-293 or 5601TRR-379.

All patents, patent applications, provisional applications, and publications referred to or cited herein are incorporated by reference in their entirety, including all figures and tables, to the extent they are not inconsistent with the explicit teachings of this specification.

TABLE 1

Linkage group, map position, locus, and base-pair lengths for soybean DNA amplified with 91 primers over 19 linkage groups.

| LG | cM Position in LG | SSR locus | TYPE | ESSEX | WILLIAMS82 | 5601T | ALLEN | 5601T RR-293 | 5601T RR-379 |
|---|---|---|---|---|---|---|---|---|---|
| A1 | 25.56 | Satt593 | EX | 188 | 185 | 188 | 188 | 188 | — |
| A1 | 31.14 | Satt591 | EX | 172 | 184 | 172 | 172 | 172 | 172 |
| A1 | 93.23 | Satt236 | WM | 214 | 226 | 226 | 226 | 226 | 226 |
| A2 | 36.77 | Satt177 | NP | 110 | 110 | 110 | 110 | 110 | 110 |
| A2 | 107.05 | Satt437 | NP | 262 | 262 | 262 | 262 | 262 | 262 |
| A2 | 125.38 | Satt133 | NP | 178 | 178 | 178 | — | 178 | 178 |
| B2 | 17.77 | Satt467 | NP | 168 | — | 168 | 168 | 168 | 168 |
| B2 | 51.49 | Satt083 | NP | 104 | 104 | 104 | 104 | 104 | 104 |
| B2 | 55.20 | Satt168 | TN | 224 | 224 | 224, 230 | 224 | 224 | 224 |
| B2 | 72.81 | Satt070 | TN | 147 | 175 | 147, 162 | 162 | 162 | 162 |
| B2 | 75.35 | Satt474 | EX | 237 | 259 | 237 | 259 | 259 | 259 |
| B2 | 87.59 | Satt534 | EX | 189 | 186 | 189 | 189 | 189 | 186, 189 |
| B2 | 113.61 | Satt687 | NP | 165 | 165 | 165 | 165 | 165 | 165 |
| C1 | 74.46 | Satt139 | EX | 229 | 183 | 229 | 229 | 229 | 229 |
| C2 | 112.19 | Satt557 | EX | 198 | 207 | 198, 201 | 198 | 198 | 198 |
| C2 | 113.96 | Satt100 | EX | 145 | 165 | 145 | 145 | 145 | 145 |
| C2 | 117.77 | Satt460 | TN | 138 | 154 | 110, 138 | 140 | 140 | 140 |
| C2 | 117.87 | Satt079 | EX | 148 | 145 | 148 | 148 | 148 | 148 |
| C2 | 121.27 | Satt307 | EX | 169 | 159 | 169 | 169 | 169 | 169 |
| C2 | 126.24 | Satt202 | EX | 280 | 304 | 280 | 280 | 280 | 280 |
| D1a | 12.00 | Satt147 | HET | 189 | 171 | 171, 189 | 171 | 171 | 171 |
| D1a | 50.20 | Satt436 | TN | 246 | 243 | 204, 246 | 204 | 204 | 204 |
| D1a | 61.89 | Satt203 | EX | 181 | 216 | 181 | 181 | 181 | 181 |
| D1a | 64.69 | Satt179 | HET | 128 | 179 | 128, 179 | 182 | 179 | 182 |
| D1a | 103.37 | Satt184 | HET | 183 | 168 | 183 | 183 | 168, 183 | 168 |

TABLE 1-continued

Linkage group, map position, locus, and base-pair lengths for soybean DNA amplified with 91 primers over 19 linkage groups.

| LG | cM Position in LG | SSR locus | TYPE | ESSEX | WILLIAMS82 | 5601T | ALLEN | 5601T RR-293 | 5601T RR-379 |
|---|---|---|---|---|---|---|---|---|---|
| D1b | 75.67 | Satt537 | HET | 146 | 159 | 146, 159 | 146 | 146 | 136 |
| D1b | 87.20 | Satt546 | HET | 218 | 242 | 218, 242 | 218 | 218 | 218 |
| D1b | 100.89 | Satt172 | HET | 222 | 219 | 222, 219 | 222, 219 | 222, 219 | 222, 219 |
| D1b | 116.35 | Satt274 | EX | 203 | 190 | 197, 203 | 197, 203 | 197, 203 | 197, 203 |
| D1b | 118.62 | Satt459 | EX | 183 | 203 | 183 | 183 | 183 | 183 |
| D2 | 16.76 | Satt328 | NP | 247 | 247 | 247 | 247 | 247 | 247 |
| D2 | 24.52 | Satt458 | NP | 103 | 103 | 103 | 103 | 103 | 103 |
| D2 | 29.56 | Satt014 | EX | 277 | 259 | 277 | 277 | 277 | 277 |
| D2 | 39.35 | Satt372 | EX | 249 | 258 | 249 | 249 | 249 | 249 |
| D2 | 47.73 | Satt002 | NP | 124 | 124 | 124 | 124 | 124 | 124 |
| D2 | 80.19 | Satt461 | HET | 151 | 154 | 151, 154 | 151, 154 | 151 | 151, 154 |
| D2 | 87.25 | Satt082 | HET | 105 | 108 | 105, 108 | 105, 108 | 105 | 105, 108 |
| E | 44.27 | Satt268 | HET | 250 | 237, 258 | 250, 258 | 250 | 250, 258 | 250 |
| E | 44.76 | Satt185 | EX | 228 | 249 | 228 | 228 | 228 | 228 |
| F | 5.36 | Satt649 | HET | 213 | 231 | 213, 231 | 231, 238 | 231, 238 | 238 |
| F | 11.37 | Satt269 | HET | 340 | 252 | 252 | 340 | 340 | 340 |
| F | 15.29 | Satt348 | EX | 215 | 218 | 215 | 215 | 215 | 215 |
| F | 16.08 | Satt252 | TN | 210 | 222 | 207 | 213 | 213 | 210 |
| F | 18.13 | Satt149 | WM | 253 | 277 | 277 | 277 | 277 | 277 |
| F | 63.69 | Satt114 | HET | 77 | 105 | 77, 105 | 105 | 105 | 105 |
| F | 77.70 | Satt335 | EX | 148 | 157 | 148 | 148 | 148 | — |
| F | 82.83 | Satt362 | EX | 255 | 258 | 255 | 255 | 255 | 255 |
| F | 87.01 | Satt072 | TN | 201 | 201 | 198, 201 | 198 | 198 | 198 |
| F | 97.97 | Satt490 | EX | 284 | 297 | 284, 290 | 284 | 284 | 284 |
| F | 102.08 | Satt144 | EX | 205 | 222 | 205 | 205 | 205 | 205 |
| F | 111.89 | Satt554 | TN | 259 | 258 | 252, 261 | 261 | 261 | 261 |
| G | 12.74 | Satt570 | TN | 102 | 102 | 105 | 105 | 105 | 105 |
| G | 21.89 | Satt235 | NP | 131 | 131 | 131 | 131 | 131 | 131 |
| G | 43.38 | Satt394 | HET | 274 | 305 | 274, 305 | 274 | 274 | — |
| G | 51.69 | Satt427 | EX | 171 | 174 | 171 | 171 | 174 | 171 |
| G | 57.32 | Satt564 | EX | 172 | 162 | 172 | 172 | 172 | 172 |
| H | 89.52 | Satt317 | HET | 263 | 248 | 248, 263 | 248 | 248 | — |
| I | 82.78 | Satt292 | TN | 247 | 235 | 220, 235 | 220 | 220 | 220 |
| J | 12.33 | Satt249 | NP | 251 | 251 | 251, 257 | 251 | 251 | 251 |
| J | 43.11 | Satt380 | TN | 135 | 135 | 127, 135 | 135 | 135 | 135 |
| K | 1.80 | Satt539 | EX | 157 | 163 | 157 | 157 | 157 | 157 |
| K | 46.63 | Satt518 | TN | 271 | 256 | 246, 271 | 271 | 271 | 271 |
| K | 56.62 | Satt273 | EX | 281 | 263 | 281 | 281 | 281 | 281 |
| K | 56.85 | Satt725 | EX | 203, 239 | 203, 242 | 239 | 203, 239 | 203, 239 | 203, 239 |
| K | 71.01 | Satt499 | NP | 305 | 305 | 305 | 305 | 305 | 305 |
| K | 78.68 | Satt475 | EX | 227 | 249 | 227 | 227 | 227 | 227 |
| K | 80.12 | Satt260 | HET | 256 | 229 | 229 | 256 | 216 | 216 |
| K | 104.79 | Satt196 | NP | 191 | 191 | 191, 203 | 191 | 191 | 191 |
| L | 0.00 | Satt495 | NP | 245 | 245 | 245 | 245 | 245 | 245 |
| L | 27.92 | Satt523 | EX | 183 | 165 | 183 | 183 | 183 | 183 |
| L | 34.54 | Satt313 | TN | 248 | 248 | 223 | 223 | 223 | 223 |
| L | 38.16 | Satt284 | NP | 161 | 161 | 161 | 161 | 161 | 161 |
| L | 41.00 | Satt462 | TN | 252 | 248 | 231 | 231 | 231 | 231 |
| L | 54.57 | Satt481 | HET | 134 | 146 | 134, 146 | 134 | 134 | 134 |
| L | 56.14 | Satt156 | WM | 206 | 221 | 218, 221 | 221 | 221 | 221 |

TABLE 1-continued

Linkage group, map position, locus, and base-pair lengths for soybean DNA amplified with 91 primers over 19 linkage groups.

| LG | cM Position in LG | SSR locus | TYPE | ESSEX | WILLIAMS82 | 5601T | ALLEN | 5601T RR-293 | 5601T RR-379 |
|---|---|---|---|---|---|---|---|---|---|
| L | 61.35 | Satt076 | HET | 160 | 163 | 160, 163 | 160 | 160 | 160 |
| L | 64.66 | Satt448 | NP | 266 | 266 | 266 | 266 | 266 | 266 |
| L | 66.51 | Satt166 | EX | 214 | 254 | 214 | 214 | 214 | 214 |
| L | 70.20 | Satt678 | NP | 157 | 157 | 157 | 157 | 157 | 157 |
| L | 70.36 | Satt527 | HET | 201 | 199 | 201, 198 | 201 | 201 | 201 |
| L | 71.44 | Satt561 | EX | 242 | 248 | 242 | 242 | 242 | 242 |
| L | 92.00 | Satt006 | NP | 132 | 132 | 132 | 132 | 132 | 132 |
| L | 92.66 | Satt664 | NP | 234 | 234 | 234 | 234 | 234 | 234 |
| L | 93.89 | Satt229 | TN | 202 | 227 | 202, 205 | 205 | 205 | 205 |
| M | 7.84 | Satt590 | EX | 319 | 312 | 319 | 319 | 319 | 319 |
| M | 33.47 | Satt567 | HET | 105 | 108 | 105, 108 | 105 | 105 | 105 |
| M | 35.85 | Satt540 | EX | 164 | 152 | 164 | 164 | 164 | 164 |
| N | 74.99 | Satt237 | TN | 250 | 250 | 239 | 239 | 239 | 239 |
| N | 76.49 | Satt255 | TN | 132 | 132 | 132, 135 | 135 | 135 | 132, 135 |
| O | 49.71 | Satt420 | NP | 230 | 230 | 230 | 230 | 230 | 230 |
| O | 54.20 | Satt479 | EX | 108 | 111 | 108 | 108 | 108 | 108 |

TABLE 2

Linkage group, map position, locus, and DNA sequence for forward and reverse primers.

| LG | cM Position in LG | SSR locus | Upper primer sequence (5'-->3') | Lower primer sequence (5'-->3') | SEQ ID NOs: | |
|---|---|---|---|---|---|---|
| A1 | 25.56 | Satt593 | GCGGGGTTGTTGATCTATAATGTAA | GCGGGTTTGGATTTTATAATGTGAT | 1 | 2 |
| A1 | 31.14 | Satt591 | GCGCGACCTTAATGATA | GCGCCCAAAGCTTAAAATTTAATA | 3 | 4 |
| A1 | 93.23 | Satt236 | GCGTGCTTCAAACCAACAAACAACTTA | GCGGTTTGCAGTACGTACCTAAAATAGA | 5 | 6 |
| A2 | 36.77 | Satt177 | CGTTTCATTCCCATGCCAATA | CCCGCATCTTTTTCAACCAC | 7 | 8 |
| A2 | 107.05 | Satt437 | ATCCCATTGTAGTGCATTTATAGTGACG | GCGGGTAACCTATTTTTTATGCTTCTGT | 9 | 10 |
| A2 | 125.38 | Satt133 | GCAAATGAAGAAAAGATGGATT | TAAAGCGATGGTTGAAGAAAG | 11 | 12 |
| B2 | 17.77 | Satt467 | GCGAAGAGCTACATCTAACACAATTCAA | GCGTTAAGCACGGTCATATTTTCTCATA | 13 | 14 |
| B2 | 51.49 | Satt083 | CAACACCCTAGCATAGTCA | AGCAGGTATGAAATGAAATT | 15 | 16 |
| B2 | 55.20 | Satt168 | CGCTTGCCCAAAAATTAATAGTA | CCATTCTCCAACCTCAATCTTATAT | 17 | 18 |
| B2 | 72.81 | Satt070 | TAAAAATTAAAATACTAGAAGACAAC | TGGCATTAGAAAATGATATG | 19 | 20 |
| B2 | 75.35 | Satt474 | GCGAAATTTGGAAATGACATCTTAGAA | GCGACGGGAGAAATTGGATGTGAAGAA | 21 | 22 |
| B2 | 87.59 | Satt534 | CTCCTCCTGCGCAACAACAATA | GGGGGATCTAGGCCATGAC | 23 | 24 |
| B2 | 113.61 | Satt687 | ACCGCAACTCACTCACCTT | GCGCCCAATTAACAGAAAC | 25 | 26 |
| C1 | 74.46 | Satt139 | TATTATAAAAATCAATGCGAAAGG | CTTTTTAATAAGCCCAAATAATTACAT | 27 | 28 |
| C2 | 112.19 | Satt557 | GCGGGATCCACCATGTAATATGTG | GCGCACTAACCCTTTATTGAA | 29 | 30 |
| C2 | 113.96 | Satt100 | ACCTCATTTTGGCATAAA | TTGGAAAACAAGTAATAATAACA | 31 | 32 |
| C2 | 117.77 | Satt460 | GCGCGATGGGCTGTTGGTTTTAT | GCGCATACGATTTGGCATTTTTCTATTG | 33 | 34 |
| C2 | 117.87 | Satt079 | AGTCGAAGATACACAATTAGAT | CTTTTAGACACAAATTTATCACT | 35 | 36 |
| C2 | 121.27 | Satt307 | GCGCTGGCCTTTAGAAC | GCGTTGTAGGAAATTTGAGTAGTAAG | 37 | 38 |
| C2 | 126.24 | Satt202 | GGAATGCATGAGTATTAACCTCTTAT | GGGCTAACGAACATGTAACTTATCAAC | 39 | 40 |

TABLE 2-continued

Linkage group, map position, locus, and DNA sequence for forward and reverse primers.

| LG | cM Position in LG | SSR locus | Upper primer sequence (5'-->3') | Lower primer sequence (5'-->3') | SEQ ID NOs: | |
|---|---|---|---|---|---|---|
| D1a | 12.00 | Satt147 | CCATCCCTTCCTCCAAATAGAT | CTTCCACACCCTAGTTTAGTGACAA | 41 | 42 |
| D1a | 50.20 | Satt436 | GCGTATAAAGAAAAACGAGCATATCAT | GCGCTTATAAAGGCTTGTGAAAGACACT | 43 | 44 |
| D1a | 61.89 | Satt203 | GCGTGTCTTCCCAATCCATCTAATCT | GCGACTCTGCATTTCTGAATAAATTCAC | 45 | 46 |
| D1a | 64.69 | Satt179 | GGGATTAGGTTTATGGAAGTTTATTAT | GGGTCATTAAAACGATCAGTAAGA | 47 | 48 |
| D1a | 103.37 | Satt184 | GCGCTATGTAGATTATCCAAATTACGC | GCCACTTACTGTTACTCAT | 49 | 50 |
| D1b | 75.67 | Satt537 | GCGTGTACATCAAAATGGTGTATTC | GCGGGAGGAACTTTGTCTCAGTAAT | 51 | 52 |
| D1b | 87.20 | Satt546 | TGAGCGATCAAGAAGCACTTA | TTTGGATCGCATAACACTTTA | 53 | 54 |
| D1b | 100.89 | Satt172 | AGCCTCCGGTATCACAG | CCTCCTTTCTCCCATTTT | 55 | 56 |
| D1b | 116.35 | Satt274 | GCGGGGTCAATTAGTTTTCGTCAGTT | GCGCACGGTATATAATCGAACCTAT | 57 | 58 |
| D1b | 118.62 | Satt459 | TCGTGTTAGATTTTACTGTCACATT | AACTGCATACCCTTTGTTTGAA | 59 | 60 |
| D2 | 16.76 | Satt328 | TGACCACCATGAGTTCATT | GGGGGTGGCTTTTAGATTC | 61 | 62 |
| D2 | 24.52 | Satt458 | TTGGGTTGACCGTGAGAGGGAGAA | GCGAACCACAAACAACAATCTTCA | 63 | 64 |
| D2 | 29.56 | Satt014 | TCTGGTAAACATTCAACTTTTTATTT | TCCAAATATGACATCATAAACTTCTA | 65 | 66 |
| D2 | 39.35 | Satt372 | CAGAAAAGGAATAATAACAACATCAC | GCGAAAACATAATTCACACAAAAGACAG | 67 | 68 |
| D2 | 47.73 | Satt002 | TGTGGGTAAAATAGATAAAAAT | TCATTTTGAATCGTTGAA | 69 | 70 |
| D2 | 80.19 | Satt461 | AAATACAAGCTTTAATAAAGTGCAGA | CTTACGTTTCCATAGATTTCTCG | 71 | 72 |
| D2 | 87.25 | Satt082 | AATTCATTTAGGGAGTTGAT | CTAGCCAATGTCATATGACT | 73 | 74 |
| E | 44.27 | Satt268 | TCAGGGGTGGACCTATATAAAATA | CAGTGGTGGCAGATGTAGAA | 75 | 76 |
| E | 44.76 | Satt185 | GCGCATATGAATAGGTAAGTTGCACTAA | GCGTTTTCCTACAATAATATTTCAT | 77 | 78 |
| F | 5.36 | Satt649 | TTACTGGCCGTGTTTACCCGTGTAA | GCGGACGTTATAAGATTTTTTTATCATG | 79 | 80 |
| F | 11.37 | Satt269 | GCGTGCCAGGTAGAAAAATATTAG | GCGGTTTTTCACTTTTCAAAATTC | 81 | 82 |
| F | 15.29 | Satt348 | GCGCTTAGTAATGGTTCCCACAGATAA | GCGGTGATATCTAGCAACACAA | 83 | 84 |
| F | 16.08 | Satt252 | GCGAATTTGGATTAATTAAATTTATG | GCGCTCGGTCCTCTCAAATAAGGTCTC | 85 | 86 |
| F | 18.13 | Satt149 | TTGCACATTCTTTTTGGTAAACAGTCATAA | GTTGGAGGCCATAGTCACATTAATCTTAGA | 87 | 88 |
| F | 63.69 | Satt114 | GGGTTATCCTCCCCAATA | ATATGGGATGATAAGGTGAAA | 89 | 90 |
| F | 77.70 | Satt335 | CAAGCTCAAGCCTCACACAT | TGACCAGAGTCCAAAGTTCATC | 91 | 92 |
| F | 82.83 | Satt362 | GCGTTGTTGTTTCAAATGTATTTTAGTT | GCGGACGGATCATCAAACCAATCAAGAC | 93 | 94 |
| F | 87.01 | Satt072 | GGAAAGAATCAGCAAAAT | CCCCCACATAAATAATAAA | 95 | 96 |
| F | 97.97 | Satt490 | GCGGCACGAGTCAACTTTCTGTTTCCT | GCGGAAGAAGATTTTCGTTTTTAT | 97 | 98 |
| F | 102.08 | Satt144 | CGTCGCCATCACTATGAGAA | CCATCTTGAGCAGAGTTTGAAGTT | 99 | 100 |
| F | 111.89 | Satt554 | GCGATATGCTTTGTAAGAAAATTA | GCGCAAGCCCAAATATTACAAATT | 101 | 102 |
| G | 12.74 | Satt570 | CTCATGTGGTCCTACCCAGACTCA | CGCTATCCCTTTGTATTTTCTTTTGC | 103 | 104 |
| G | 21.89 | Satt235 | GCGGGCTTTGCCAAGAAGTTT | GCGGTGAGGCTGGCTATAAG | 105 | 106 |
| G | 43.38 | Satt394 | GCGTTTTTTCAATTTAAAGAGAATTGAC | GCGTAACTTGCATGTGTATATCGAGATG | 107 | 108 |
| G | 51.69 | Satt427 | GCGAGTATCCACCCTTTTATAATAAT | TCTCCACGCCACCTTATTTCCTCTCC | 109 | 110 |
| G | 57.32 | Satt564 | GCGCTTCCACCACAATAACA | GCGGCAGAGGACTGACAGCTA | 111 | 112 |

TABLE 2-continued

Linkage group, map position, locus, and DNA sequence for forward and reverse primers.

| LG | cM Position in LG | SSR locus | Upper primer sequence (5'-->3') | Lower primer sequence (5'-->3') | SEQ ID NOs: |
|---|---|---|---|---|---|
| H | 89.52 | Satt317 | GCGAACAAACTTTCTATACATGATAACA | GCGGGTATATTTTTGTACATAAGTTGGAA | 113 114 |
| I | 82.78 | Satt292 | GCGGAATTAGAACTCCAGTAAAGA | GCGAGGCCAACATTGAAAAGT | 115 116 |
| J | 12.33 | Satt249 | GCGGCAAATTGTTATTGTGAGAC | GGCCAGTGTTGAGGGATTTAGA | 117 118 |
| J | 43.11 | Satt380 | GCGAGTAACGGTCTTCTAACAAGGAAAG | GCGTGCCCTTACTCTCAAAAAAAAA | 119 120 |
| K | 1.80 | Satt539 | GCGGTTGTAATTTAATGAACACATT | GCGGATTTTGGACTGGATTAAATAA | 121 122 |
| K | 46.63 | Satt518 | GCGCATATCAAATTGCATATAAAAATACG | GCGGGAATATAAAATAAAAATGCTCACTT | 123 124 |
| K | 56.62 | Satt273 | GCGCCTGATTACATTATCGCTTA | GCCTTTCGTTCTCAAACTGAGAGT | 125 126 |
| K | 56.85 | Satt725 | GCGATAGAGCAACTGGCAAACTTGAT | GCGAATGGAGAAAATATGGACAAAA | 127 128 |
| K | 71.01 | Satt499 | GCGGCAGAGATAATTGTATTTTTG | GCGCTGCCCACTAGGGAACGAAAGATGA | 129 130 |
| K | 78.68 | Satt475 | AAATGCAACTTACACAACTTTAT | TGCTTGCTTCAATTTGGATGAGTG | 131 132 |
| K | 80.12 | Satt260 | GCGCCAAATGTATACTTTAAATTCTT | GCGGGTTTAGCTAAAATAGTTCGTGC | 133 134 |
| K | 104.79 | Satt196 | TTGGGAAATAGTGATTGAGGTAAAA | AAATCCCCATTGAATGAGAATAAG | 135 136 |
| L | 0.00 | Satt495 | TGCCGCGAGATTAATATAATTTGT | GTGCGGCAAGAAGTTGAAATAAAG | 137 138 |
| L | 27.92 | Satt523 | GCGATTTCTTCCTTGAAGAATTTTCTG | GCGCTTTTTCGGCTGTTATTTTTAACT | 139 140 |
| L | 34.54 | Satt313 | GCGGTAAGTCATGGCTTTTTAATCTT | GCGCGAGGTATGGAACCTAACTCACA | 141 142 |
| L | 38.16 | Satt284 | TGGGCTAGGAGTGACCAC | GGTCACCACTCACCATCA | 143 144 |
| L | 41.00 | Satt462 | GCGGTCACGAATACAAGATAAATAATGC | GCGTGCATGTCAGAAAAAATCTCTATAA | 145 146 |
| L | 54.57 | Satt481 | GGGTTAACCGTCCACACATCTATT | DACGGTTTTAAACGGTAAGAAAAT | 147 148 |
| L | 56.14 | Satt156 | CGCACCCCTCATCCTATGTA | CCAACTAATCCCAGGGACTTACTT | 149 150 |
| L | 61.35 | Satt076 | TAATCGAGATTAATAGAAAACA | TGGATGGACATTTTCAG | 151 152 |
| L | 64.66 | Satt448 | GCGCTAAGGGCAATTTTATTCAA | GCGCAGCCTGTTCAGTTTTTCTTTTGTC | 153 154 |
| L | 66.51 | Satt166 | TTGCACAGTTGATTTTTGTTT | GCATCGAATTTCTGGATTTAC | 155 156 |
| L | 70.20 | Satt678 | CTAAGCGTGACAAACAGACCATTA | CGGCCATATCTACCAATCAGA | 157 158 |
| L | 70.36 | Satt527 | GCGGTTACATCTTGCAAACTAAATTAAC | GCGGAATTTTGCACATAAATTAATAACT | 159 160 |
| L | 71.44 | Satt561 | GCGGACGAATTTTCCAGA | GCGGGCAACAATATTTGAATCTA | 161 162 |
| L | 92.00 | Satt006 | CAATGTGATTAGTTTTGGAAA | GGGTTAATGTTGTTTTTTATA | 163 164 |
| L | 92.66 | Satt664 | GCGTAGATGCTCAACATCAACACTAATCTG | GCGGACGATGAAGAAATATACTATTACGAA | 165 166 |
| L | 93.89 | Satt229 | TGGCAGCACACCTGCTAAGGGAATAAA | GCGAGGTGGTCTAAAATTATTACCTAT | 167 168 |
| M | 7.84 | Satt590 | GCGCGCATTTTTTAAGTTAATGTTCT | GCGCGAGTTAGCGAATTATTTGTC | 169 170 |
| M | 33.47 | Satt567 | GGCTAACCCGCTCTATGT | GGGCCATGCACCTGCTACT | 171 172 |
| M | 35.85 | Satt540 | CTGGCGAATCAAGCTTTGTAAC | CCGTGATTGCGAAGAGGATATT | 173 174 |
| N | 74.99 | Satt237 | GCGTGATTTCAATCCTTTTC | GCGGTTGTCCTGTTAGAACCT | 175 176 |
| N | 76.49 | Satt255 | GCGCTTTTAGCGTCGTCTGGC | TACCCCTCTCTTATTCTTCTT | 177 178 |
| O | 49.71 | Satt420 | GCGTATTCAGCAAAAAAATATCAA | TTATCGCACGTGTAAGGAGACAAAT | 179 180 |
| O | 54.20 | Satt479 | GCGCTTTCAAAAAGTAACAATTAATGAAA | GCGGGAATTGGTTAATCTCATCGTGAC | 181 182 |

REFERENCES

U.S. Pat. No. 4,761,373
U.S. Pat. No. 4,810,648
U.S. Pat. No. 5,008,200
U.S. Pat. No. 5,013,659
U.S. Pat. No. 5,024,944
U.S. Pat. No. 5,126,133
U.S. Pat. No. 5,141,870
U.S. Pat. No. 5,188,960
U.S. Pat. No. 5,304,732
U.S. Pat. No. 5,331,107
U.S. Pat. No. 5,378,824
U.S. Pat. No. 5,559,223
U.S. Pat. No. 5,605,011
U.S. Pat. No. 5,731,180
U.S. Pat. No. 5,767,361
U.S. Pat. No. 5,850,016
U.S. Pat. No. 5,885,801
U.S. Pat. No. 5,885,802
U.S. Pat. No. 5,912,414
U.S. Pat. No. 5,928,937
U.S. Pat. No. 5,939,599
U.S. Pat. No. 5,990,389
U.S. Pat. No. 6,063,947
U.S. Pat. No. 6,080,913
U.S. Pat. No. 6,096,708
U.S. Pat. No. 6,127,600
U.S. Pat. No. 6,323,392
U.S. Pat. No. 6,346,403
U.S. Pat. No. 6,372,976
U.S. Pat. No. 6,441,274
U.S. Pat. No. 6,459,019
U.S. Pat. No. 6,531,648
U.S. Pat. No. 6,573,240
U.S. Pat. No. 6,664,445
U.S. Pat. No. 6,737,273
U.S. Pat. No. 6,787,683
U.S. Pat. No. 6,858,778
U.S. Pat. No. 7,138,568
U.S. Patent Application Publication 2004/0034886
WO 93/11245
WO 99/64579
WO 01/12800
WO 00/68393
WO 03/082899

Aono, M. et al. "Paraquat Tolerance of Transgenic *Nicotiana tabacum* with Enhanced Activities of Glutathione Reductase and Superoxide Dismutase", *Plant Cell Physiol.*, 1995, pp. 1687-1691, Vol. 36.

Datta, S. K. et al. "Herbicide-resistant Indica rice plants from IRRI breeding line IR72 after PEG-mediated transformation of protoplasts" *Plant Mol Biol*, November 1992, pp. 619-629, Vol. 20, No. 4.

Elliot, K. J. et al. "Isolation and characterization of fruit vacuolar invertase genes from two tomato species and temporal differences in mRNA levels during fruit ripening", *Plant Molec. Biol.*, February 1993, pp. 515-524, Vol. 21, No. 3.

Fisher, D. K. et al. "Starch Branching Enzyme II from Maize Endosperm", *Plant Physiol.*, December 1993, pp. 1045-1046, Vol. 102.

Hammock, B. D. et al. "Expression and effects of the juvenile hormone esterase in a baculovirus vector", *Nature*, Mar. 29, 1990, pp. 458-461, Vol. 344.

Hattori, J. et al. "An acetohydroxy acid synthase mutant reveals a single site involved in multiple herbicide resistance", *Mol Gen Genet.*, July 1995, pp. 419, Vol. 246, No. 4.

Frisch, M., M. Bohn, A. E. Melchinger (1999) "Comparison of Selection Strategies for Marker-Assisted Backcrossing of a Gene" *Crop Sci.* 39:1295-1301.

Hillel, J., T. Schaap, A. Haberfeld, A. J. Jeffreys, Y. Plotzky, A. Cahaner, U. Lavi (1990) "DNA Fingerprints Applied to Gene Introgression in Breeding Programs" *Genetics* 124: 783-789.

Hospital, F., C. Chevalet, P. Mulsant (1992) "Using Markers in Gene Introgression Breeding Programs" *Genetics* 132: 1199-1210.

Knutzon, D. S. et al. "Modification of *Brassica* Seed Oil by Antisense Expression of a Stearoyl-Acyl Carrier Protein Desaturase Gene", *Proc. Natl. Acad. Sci. USA, Apr.* 1, 1992, pp. 2624-2628, Vol. 89, No. 7.

Lee, K. Y. et al. "The molecular basis of sulfonylurea herbicide resistance in tobacco", *EMBO J., May* 1988, pp. 1241-1248, Vol. 7, No. 5.

Miki, B. L. et al. "Transformation of *Brassica napus* canola cultivars with *Arabidopsis thaliana* acetohydroxy acid synthase genes and analysis of herbicide resistance", *Theor. Appl. Genet., October* 1990, pp. 449-458, Vol. 80, No. 4.

Openshaw, S. J., S. G. Jarboe, and W. D. Beavis (1994) Marker-Assisted Selection in Backcross Breeding. In Proceedings of the Symposium "Analysis of Molecular Marker Data", Corvallis, Oreg., 5-6 Aug. 1994. Am. Soc. Hortic. Sci. and Crop Sci. Soc. Am.

Pantalone, V. R., F. L. Allen, D. Landau-Ellis (2003a) "Registration of '5601T' soybean" *Crop Sci.* 43:1123-1124.

Pantalone, V. R., F. L. Allen, D. Landau-Ellis (2003b) "Registration of TN93-99 soybean gennplasm" *Crop Sci.* 43:1137.

Pen, J. et al. "Production of Active *Bacillus licheniformis* Alpha-Amylase in Tobacco and its Application in Starch Liquefaction", *Bio/Technology*, March 1992, pp. 292-296, Vol. 10, No. 3.

Shiota, N. et al. "Herbicide-Resistant Tobacco Plants Expressing the Fused Enzyme between Rat Cytochrome P4501A1 (CYP1A1) and Yeast NADPH-Cytochrome P450 Oxidoreductase", *Plant Physiol.*, September 1994, pp. 17-23, Vol. 106, No. 1.

Shiroza, T. et al. "Sequence analysis of the *Streptococcus mutans* fructosyltransferase gene and flanking regions", *J. Bacteriol.*, February 1988, pp. 810-816, Vol. 170, No. 2.

Sogaard, M et al. "Site-directed mutagenesis of histidine 93, aspartic acid 180, glutamic acid 205, histidine 290, and aspartic acid 291 at the active site and tryptophan 279 at the raw starch binding site in barley alpha-amylase 1 ", *J. Biol. Chem.*, Oct. 25, 1993, pp. 22480-22484, Vol. 268, No. 30.

Steinmetz, M. et al. "The DNA Sequence of the Gene for the Secreted *Bacillus Subtilis* Enzyme Levansucrase and Its Genetic Control Sites", *Mol. Gen. Genet.*, July 1985, pp. 220-228, Vol. 200, No. 2.

We claim:

1. A composition of matter comprising:
    (a) a seed of soybean variety 5601TRR-292, representative seed of said soybean variety 5601TRR-292 having been deposited with the National Collection of Industrial, Marine and Food Bacteria under Accession number NCIMB 41461;
    (b) a soybean plant, or a part thereof, produced by growing the seed of (a);
    (c) a soybean plant, or a part thereof, produced by growing the seed of (a), wherein the part is pollen or an ovule;
    (d) a soybean plant, or a part thereof, expressing all the physiological and morphological characteristics of soybean variety 5601TRR-292, representative seed of said soybean variety having been deposited with the National Collection of Industrial, Marine and Food Bacteria under Accession number NCIMB 41461;
    (e) a tissue culture produced from the cells or protoplasts obtained from the plant of (b);
    (f) a tissue culture produced from the cells or protoplasts obtained from the plant of (b), cells or protoplasts are produced from a plant tissue selected from the group consisting of: leaf, pollen, cotyledon, hypocotyl, embryos, root, pod, flower, shoot and stem;
    (g) a soybean plant regenerated from tissue culture and having all the morphological and physiological characteristics of soybean variety 5601TRR-292, representative seed of said soybean variety 5601TRR-292 having been deposited with the National Collection of Industrial, Marine and Food Bacteria under Accession number NCIMB 41461; or
    (h) a soybean plant, or a part thereof, produced by growing the seed of (a) and transformed with a transgene conferring additional herbicide resistance, conferring pest or insect resistance, conferring drought or freeze tolerance, conferring altered carbohydrate or antioxidant content, conferring disease resistance, or conferring altered amino acid or fatty acid content.

2. The composition of matter according to claim 1, wherein said composition of matter is the soybean plant of claim 1(h) and the transgene confers resistance to a herbicide selected from the group consisting of sulfonylurea, imidazolinone, glufosinate, phenoxy proprionic acid, cyclohexone, triazine, and benzonitrile.

3. A method for producing a soybean seed comprising crossing two soybean plants and harvesting the resultant soybean seed, wherein at least one soybean plant is a soybean plant, or a part thereof, produced by growing the seed of soybean variety 5601TRR-292, representative seed of said soybean variety 5601TRR-292 having been deposited with the National Collection of Industrial, Marine and Food Bacteria under Accession number NCIMB 41461.

4. A method for producing hybrid soybean seed comprising crossing the soybean plant grown from a seed of soybean variety 5601TRR-292, representative seed of said soybean variety 5601TRR-292 having been deposited with the National Collection of Industrial, Marine and Food Bacteria under Accession number NCIMB 41461, with a second soybean plant and harvesting the resultant hybrid soybean seed.

5. A method for producing a 5601TRR-292 derived soybean plant, comprising:
   a) crossing soybean variety 5601TRR-292, a sample of said soybean variety seed having been deposited with the National Collection of Industrial, Marine and Food Bacteria under Accession number NCIMB 41461, with a second soybean plant to yield progeny soybean seed; and
   b) growing said progeny soybean seed to yield said 5601TRR-292 derived soybean plant.

6. The method of claim 5, wherein the second soybean plant is transgenic.

7. A method of producing a transgenic soybean plant comprising introducing a transgene into a soybean plant grown from the seed of soybean variety 5601TRR-292, representative seed of said soybean variety 5601TRR-292 having been deposited with the National Collection of Industrial, Marine and Food Bacteria under Accession number NCIMB 41461, wherein said transgene confers herbicide resistance; confers disease, pest or insect resistance; confers drought or freeze tolerance; or confers altered amino acid or fatty acid profile in said transgenic soybean plant.

8. The method according to claim 7, wherein the transgene confers resistance to a herbicide selected from the group consisting of sulfonylurea, imidazolinone, glufosinate, phenoxy proprionic acid, cyclohexone, triazine, and benzonitrile.

9. The method according to claim 7, wherein the transgene confers resistance to a pest.

10. The method according to claim 7, wherein the transgene confers disease resistance.

11. The method according to claim 7, wherein the transgene confers resistance to an insect.

12. The method according to claim 7, wherein the transgene confers an altered amino acid profile.

13. The method according to claim 7, wherein said transgene confers an altered fatty acid profile.

14. The method according to claim 7, wherein said transgene confers altered antioxidant content.

15. The method according to claim 7, wherein said transgene confers altered carbohydrate content.

16. The method according to claim 7, wherein said transgene confers drought tolerance.

17. The method according to claim 7, wherein said transgene confers freeze tolerance.

18. The composition of matter according to claim 1 comprising a seed of soybean variety 5601TRR-292, representative seed of said soybean variety 5601TRR-292 having been deposited with the National Collection of Industrial, Marine and Food Bacteria under Accession number NCIMB 41461.

19. The composition of matter according to claim 1 comprising a soybean plant, or a part thereof, produced by growing the seed of soybean variety 5601TRR-292, representative seed of said soybean variety 5601TRR-292 having been deposited with the National Collection of Industrial, Marine and Food Bacteria under Accession number NCIMB 41461.

20. The composition of matter according to claim 1 comprising a soybean plant, or a part thereof, produced by growing the seed of soybean variety 5601TRR-292, representative seed of said soybean variety 5601TRR-292 having been deposited with the National Collection of Industrial, Marine and Food Bacteria under Accession number NCIMB 41461, wherein the part is pollen or an ovule.

21. The composition of matter according to claim 1 comprising a soybean plant, or a part thereof, expressing all the physiological and morphological characteristics of soybean variety 5601TRR-292, representative seed of said soybean variety having been deposited with the National Collection of Industrial, Marine and Food Bacteria under Accession number NCIMB 41461.

22. The composition of matter according to claim 1 comprising a tissue culture produced from the cells or protoplasts obtained from a plant produced by growing the seed of soybean variety 5601TRR-292, representative seed of said soybean variety 5601TRR-292 having been deposited with the National Collection of Industrial, Marine and Food Bacteria under Accession number NCIMB 41461.

23. The composition of matter according to claim 1 comprising a tissue culture produced from the cells or protoplasts obtained from a plant produced by growing the seed of soybean variety 5601TRR-292, representative seed of said soybean variety 5601TRR-292 having been deposited with the National Collection of Industrial, Marine and Food Bacteria under Accession number NCIMB 41461, wherein said cells or protoplasts are produced from a plant tissue selected from the group consisting of: leaf, pollen, cotyledon, hypocotyl, embryos, root, pod, flower, shoot and stem.

24. The composition of matter according to claim 1 comprising a soybean plant regenerated from a tissue culture, said soybean plant having all the morphological and physiological characteristics of soybean variety 5601TRR-292 (Deposit No. NCIMB 41461), representative seed of said soybean variety 5601TRR-292 having been deposited with the National Collection of Industrial, Marine and Food Bacteria under Accession number NCIMB 41461.

25. The composition of matter according to claim 1 comprising a soybean plant, or a part thereof, produced by growing the seed of soybean variety 5601TRR-292, representative seed of said soybean variety 5601TRR-292 having been deposited with the National Collection of Industrial, Marine and Food Bacteria under Accession number NCIMB 41461 and transformed with a transgene conferring additional herbicide resistance, conferring pest or insect resistance, conferring drought or freeze tolerance, conferring altered carbohydrate or antioxidant content, conferring disease resistance, or conferring altered amino acid or fatty acid content.

26. The composition of matter according to claim 1, wherein said soybean variety is 5601TRR-292, representative seed of said soybean variety 5601TRR-292 having been deposited with the National Collection of Industrial, Marine and Food Bacteria under Accession number NCIMB 41461.

* * * * *